United States Patent

Marian, Jr. et al.

[11] Patent Number: 6,162,175
[45] Date of Patent: Dec. 19, 2000

[54] MULTI-ARRAY PENCIL-SIZED UNTRASOUND TRANSDUCER AND METHOD OF IMAGING AND MANUFACTURE

[75] Inventors: Vaughn R. Marian, Jr., Saratoga; Richard Demartini, Millbrae, both of Calif.

[73] Assignee: Acuson Corporation, Mountain View, Calif.

[21] Appl. No.: 09/316,486

[22] Filed: May 21, 1999

Related U.S. Application Data

[62] Division of application No. 08/939,753, Sep. 29, 1997, Pat. No. 5,957,850.

[51] Int. Cl.[7] ........................................... A61B 8/00
[52] U.S. Cl. ................................................ 600/447
[58] Field of Search ............................ 600/443, 447, 600/459, 463, 466–467; 128/916

[56] References Cited

U.S. PATENT DOCUMENTS

| | | |
|---|---|---|
| 3,888,238 | 6/1975 | Meindl et al. . |
| 4,417,583 | 11/1983 | Bechai et al. . |
| 4,483,344 | 11/1984 | Atkov et al. . |
| 4,870,867 | 10/1989 | Shaulov ................................ 600/461 |
| 5,161,537 | 11/1992 | Hashimoto et al. . |
| 5,437,283 | 8/1995 | Ranalletta et al. . |
| 5,680,863 | 10/1997 | Hossack et al. . |
| 5,776,067 | 7/1998 | Kamada et al. ...................... 600/443 |
| 5,797,848 | 8/1998 | Marian, Jr. et al. . |
| 5,876,345 | 3/1999 | Eaton et al. ........................... 600/466 |

*Primary Examiner*—Francis J. Jaworski
*Attorney, Agent, or Firm*—Brinks Hofer Gilson & Lione

[57] ABSTRACT

An ultrasound transducer having a field of view greater than 180°, and having a physical shape which permits it to be employed in the investigation and observation of the anatomy, or other body, object or region of interest, having limited access. A plurality of ultrasound transducer arrays are provided, each having a field of view defining an image plane, wherein the axis of each transducer array lies within its corresponding defined image plane. Preferably, the plurality of transducer arrays are positioned end-to-end and nonaxially aligned with the image planes of all transducer arrays coincident, and with each transducer array having a field of view of about 90°, whereby a resulting combined field of view greater than 90° is produced.

8 Claims, 20 Drawing Sheets

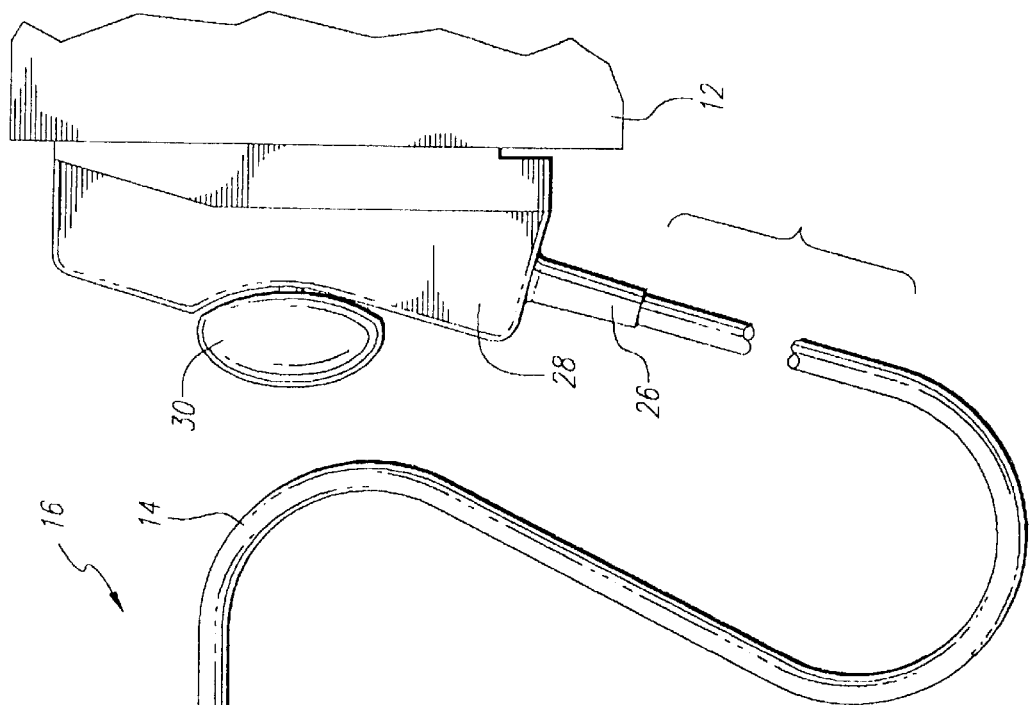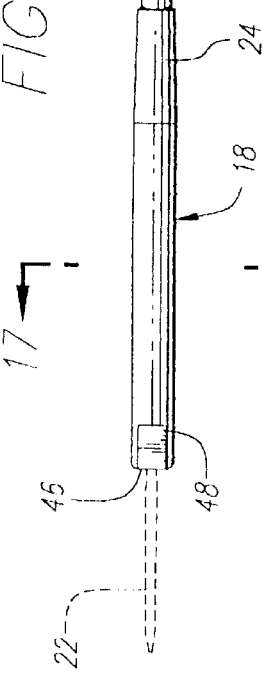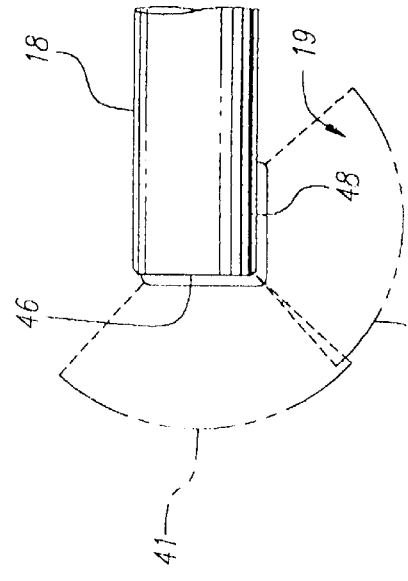

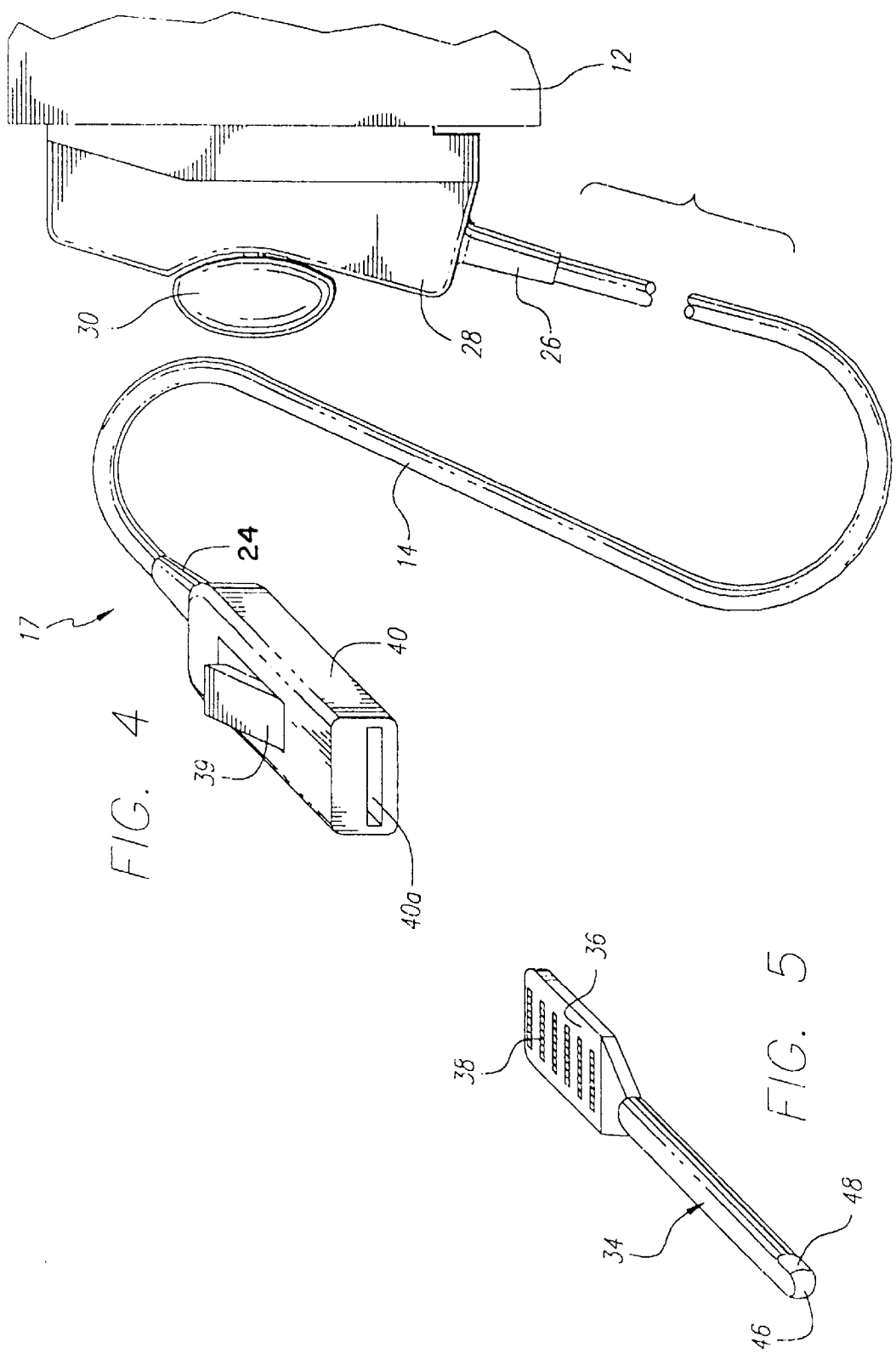

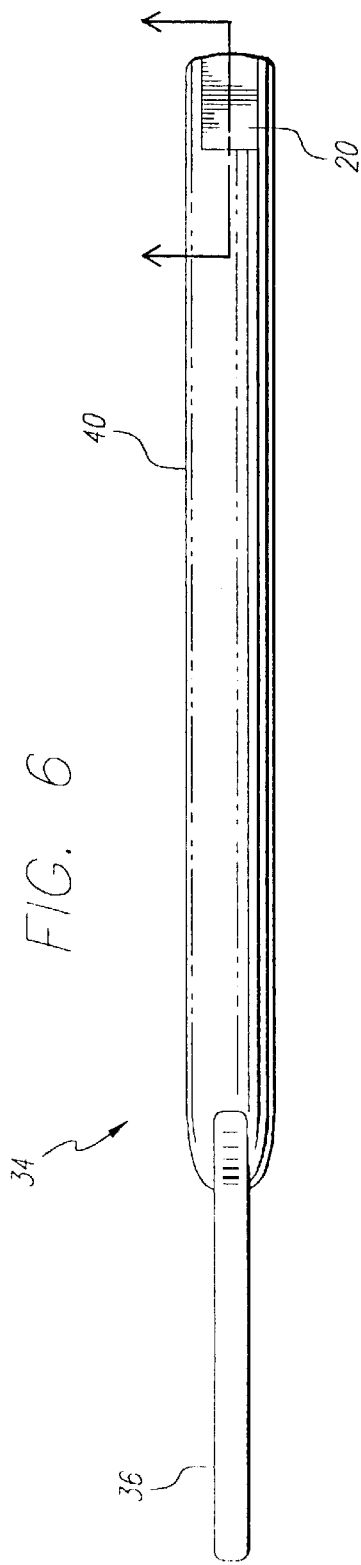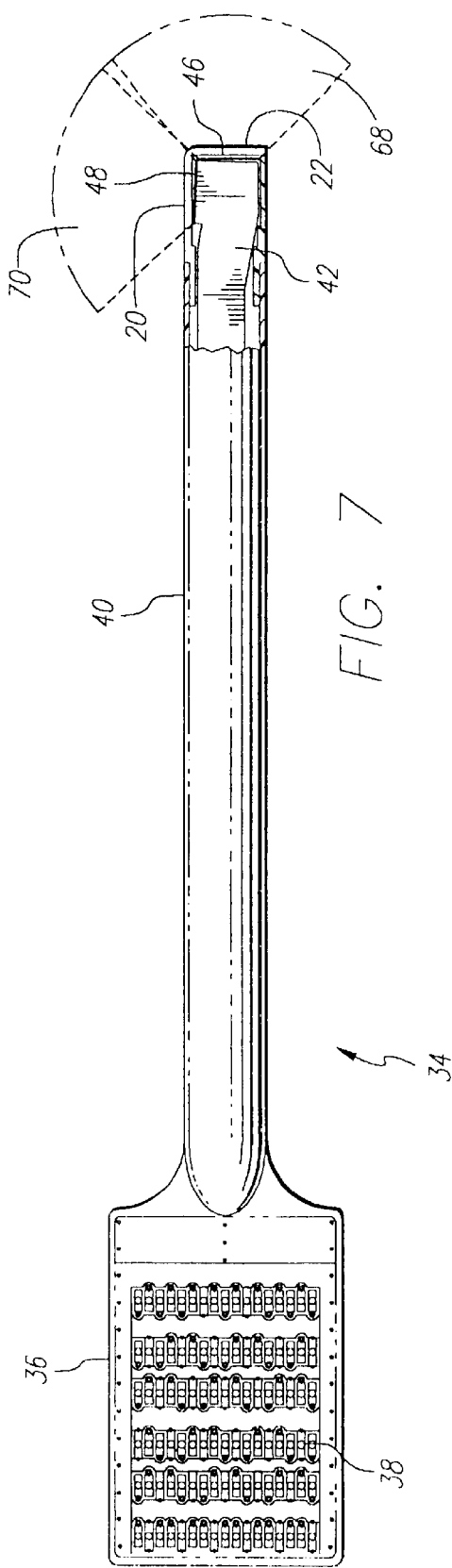
FIG. 6
FIG. 7

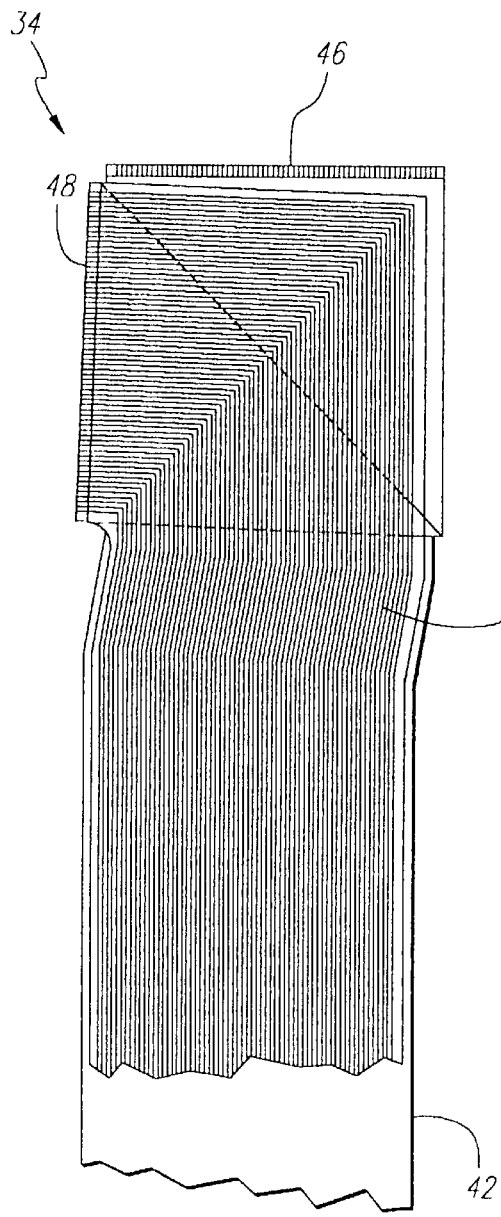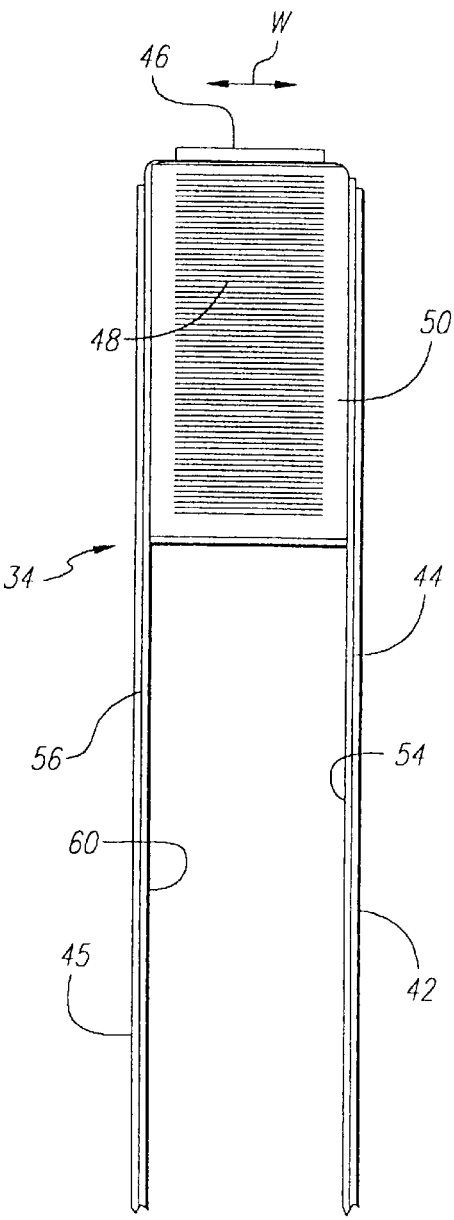
FIG. 15
FIG. 16

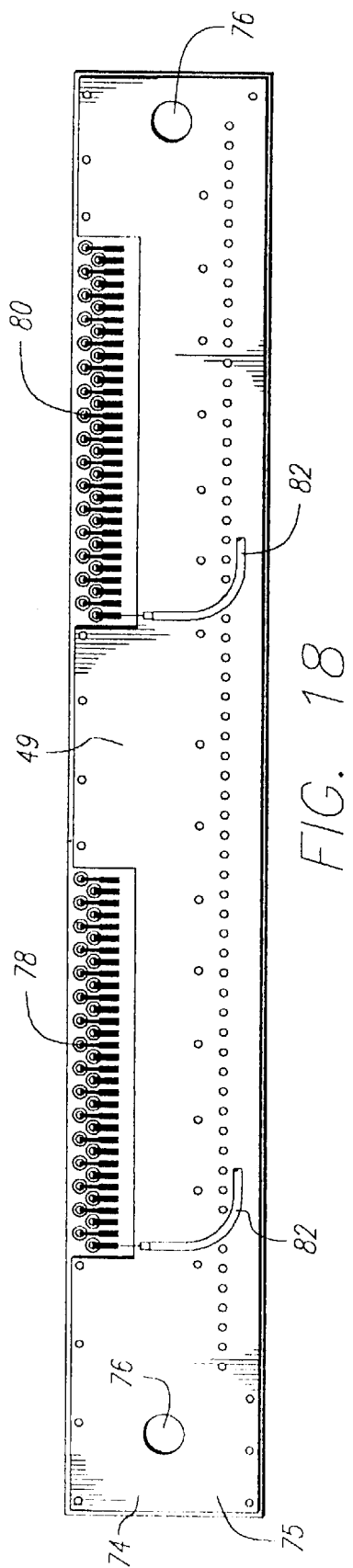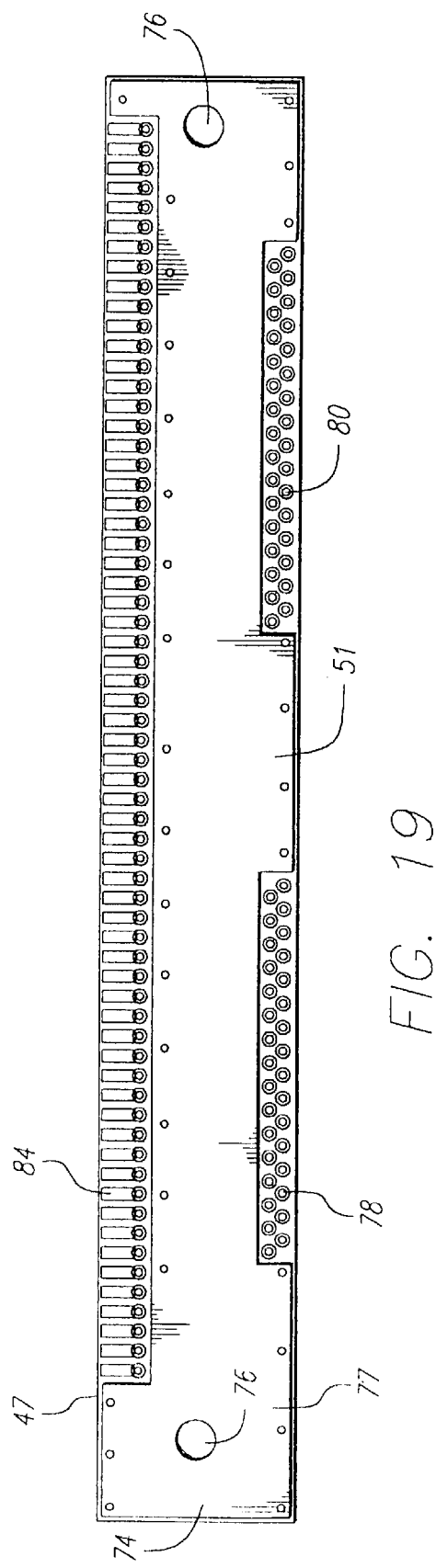

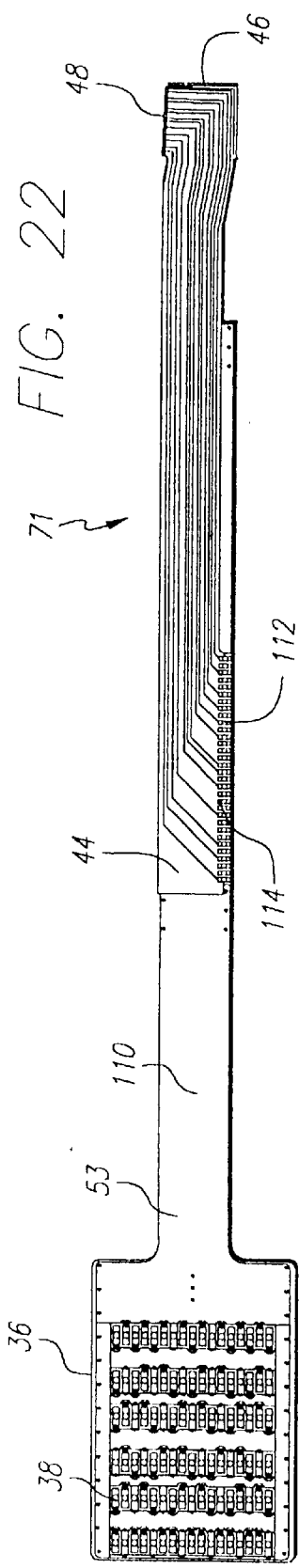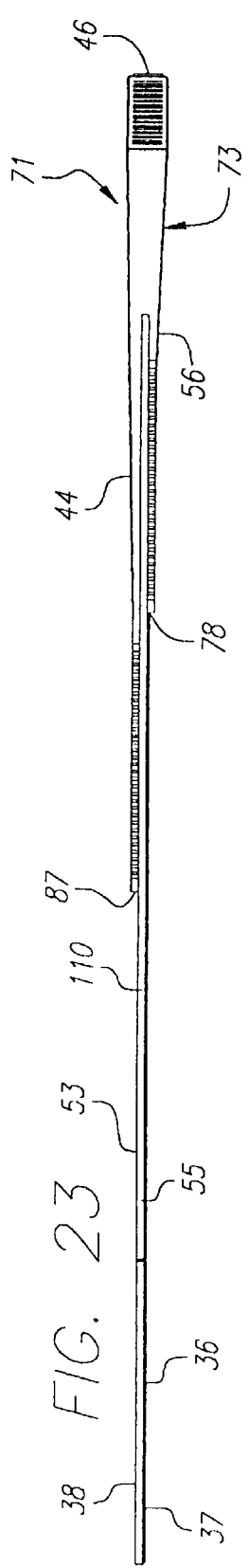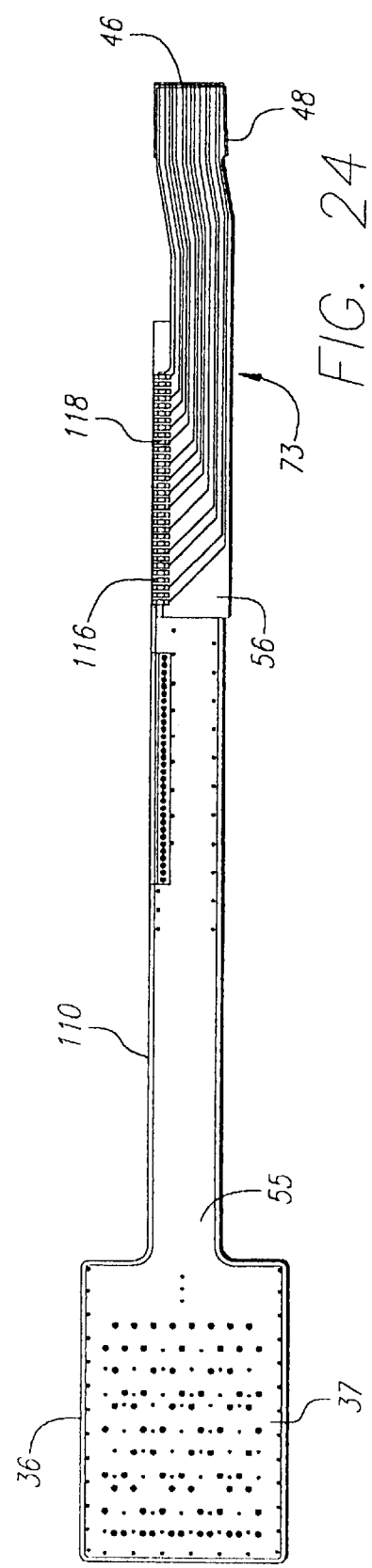

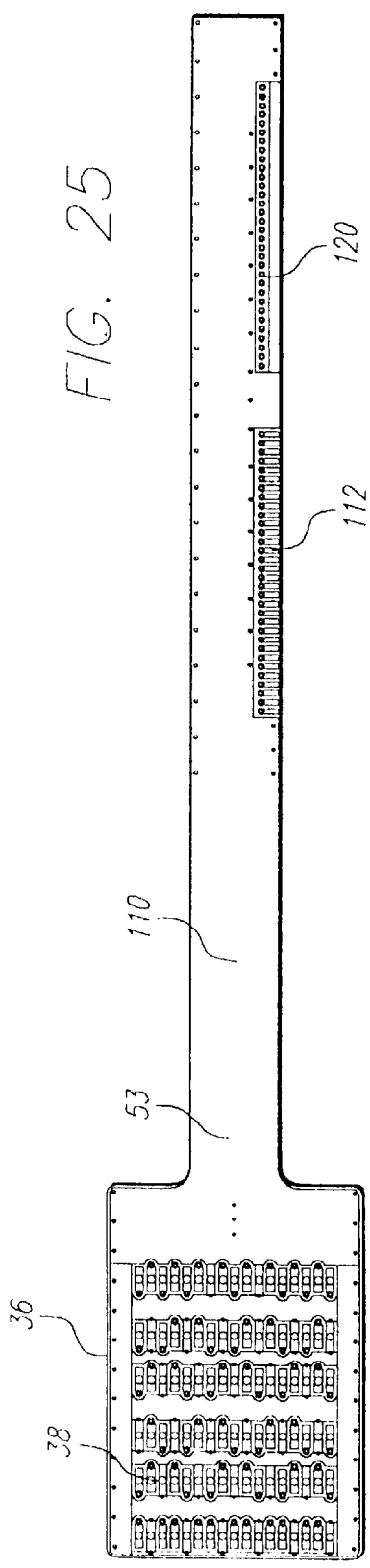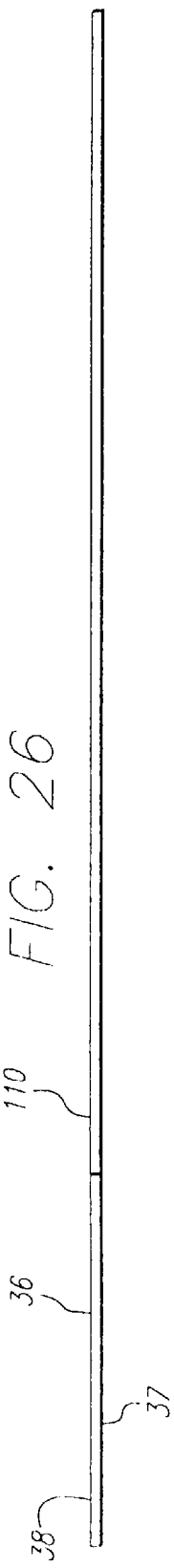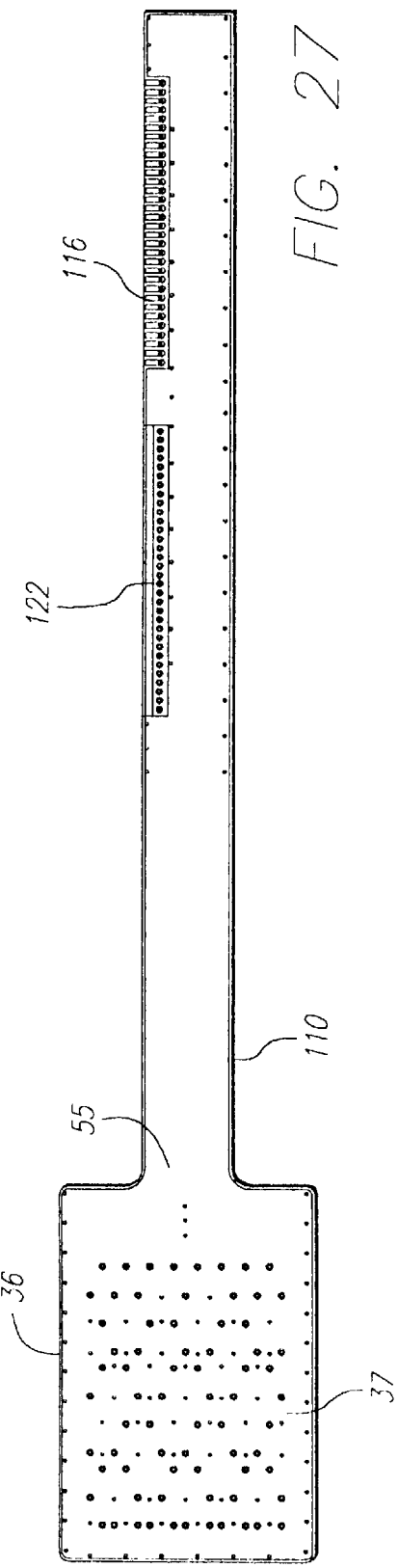

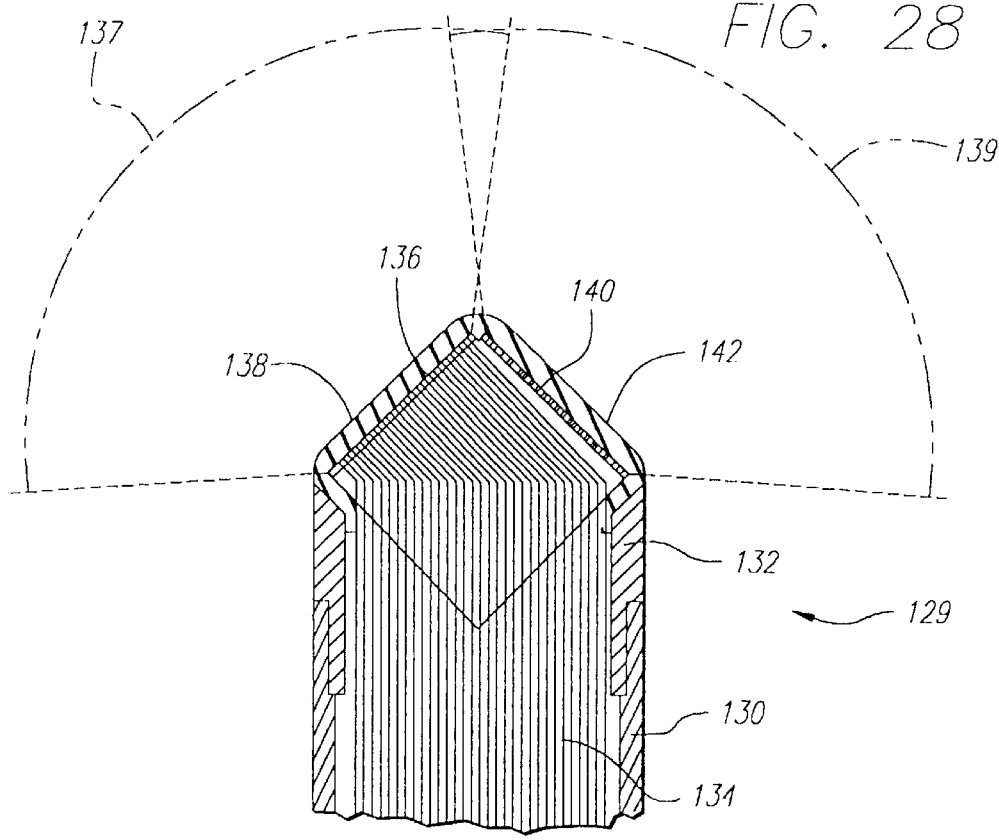
FIG. 28
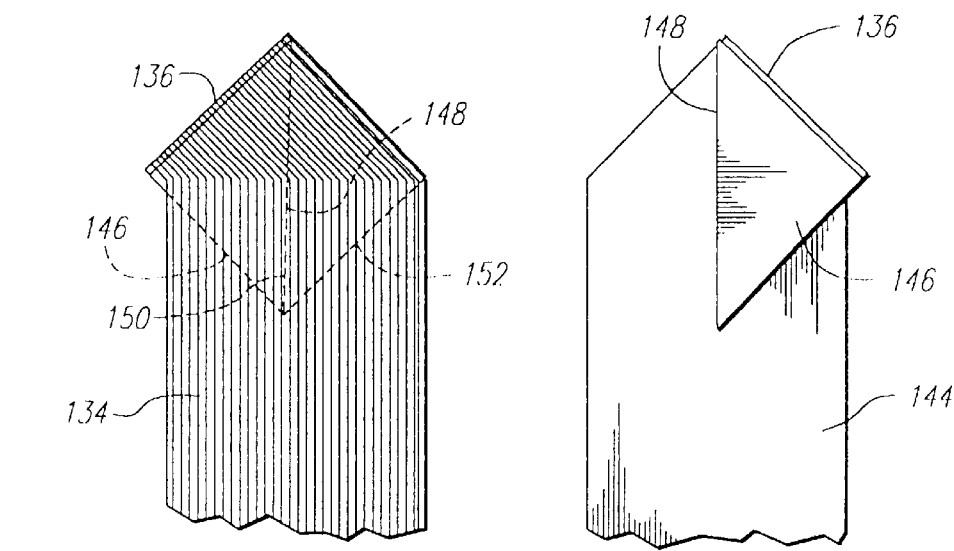
FIG. 29
FIG. 30

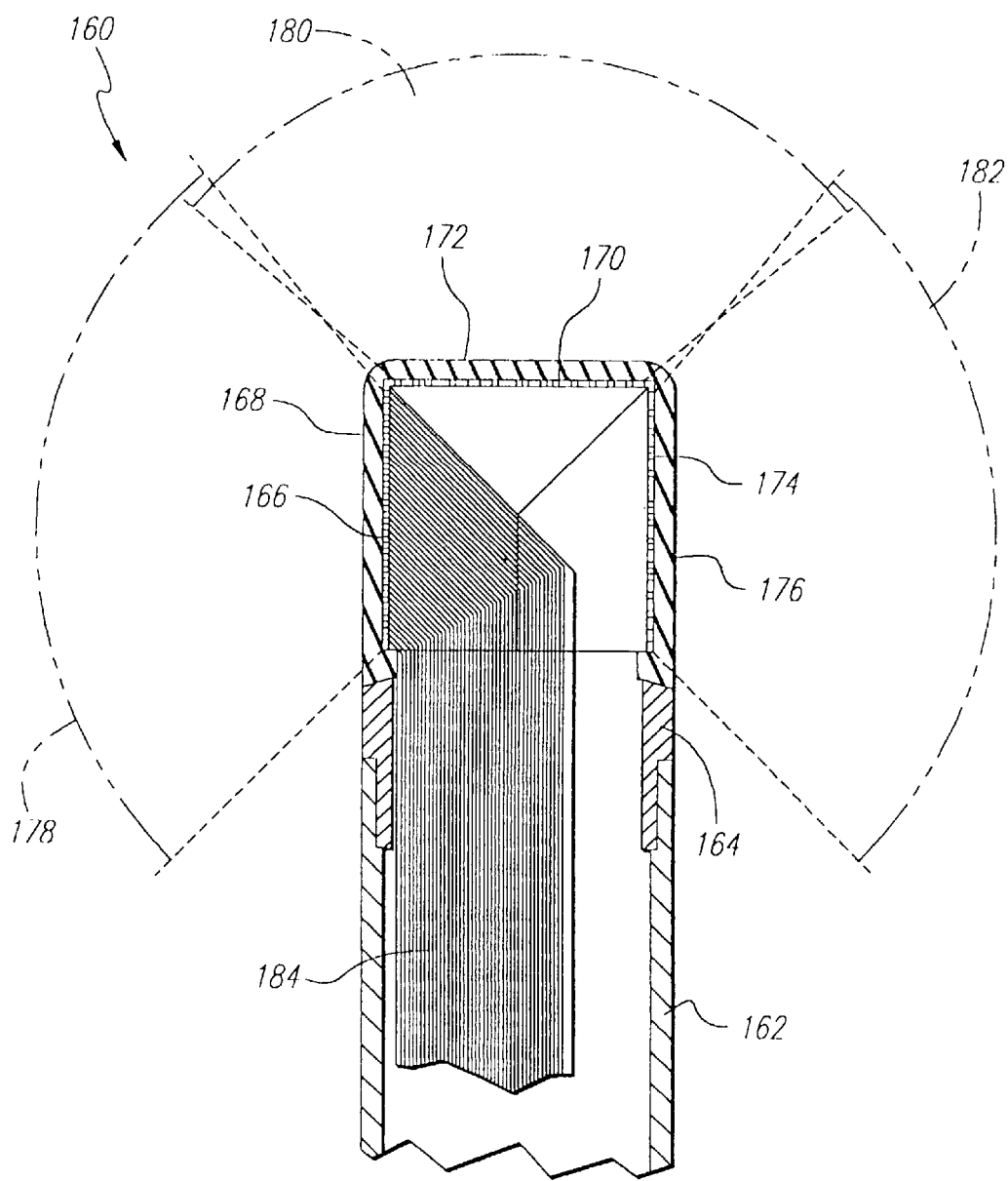

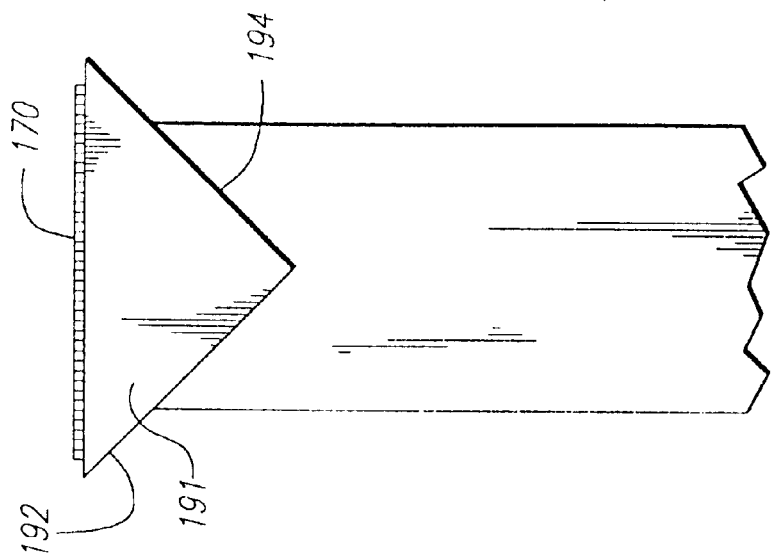
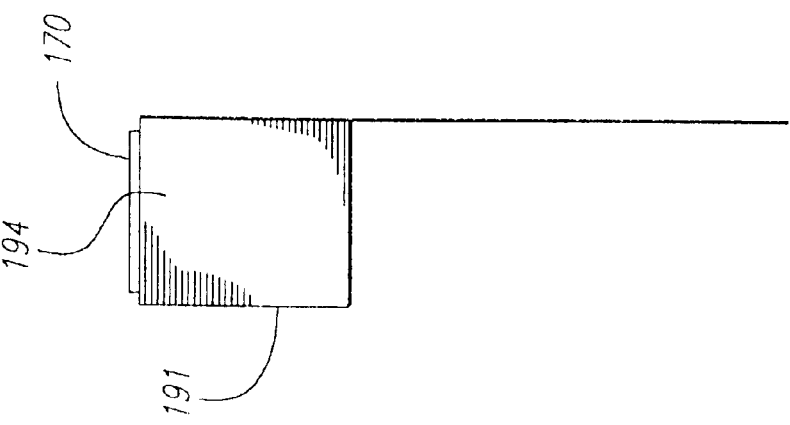
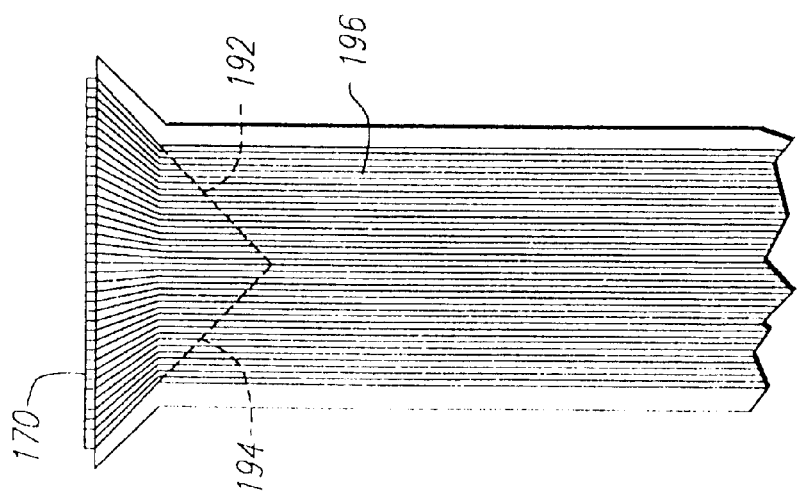

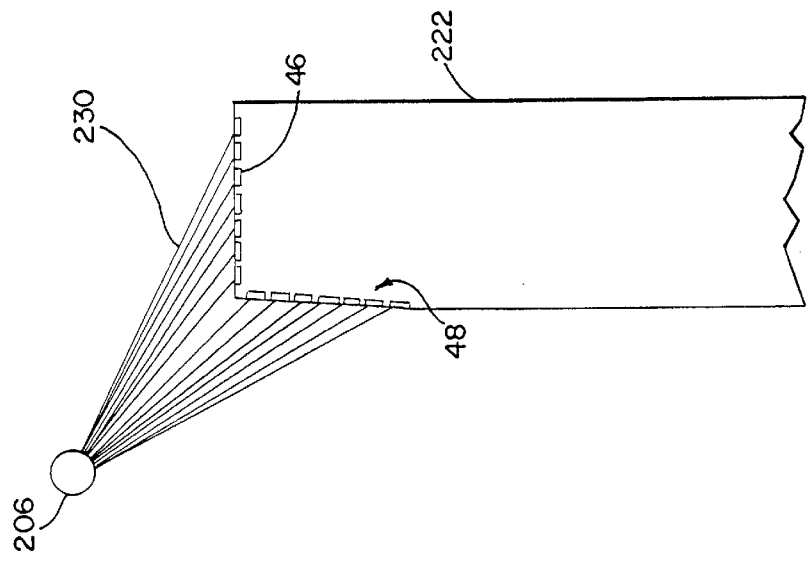
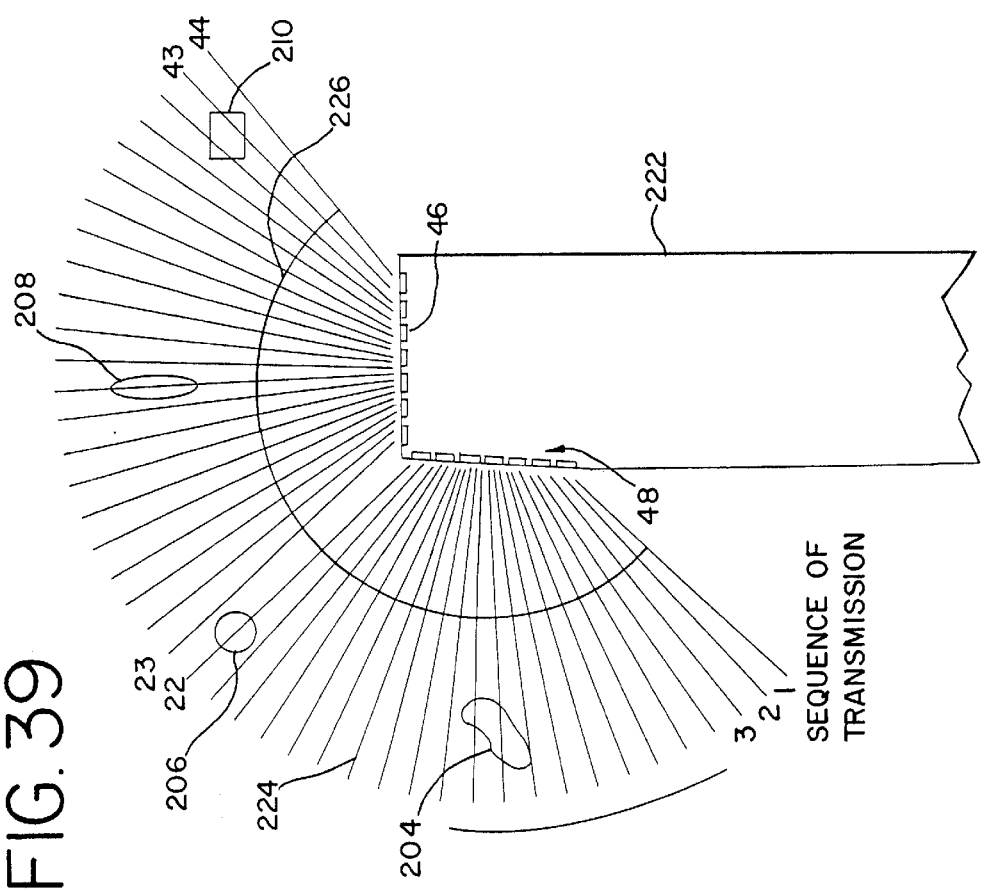

MULTI-ARRAY PENCIL-SIZED UNTRASOUND TRANSDUCER AND METHOD OF IMAGING AND MANUFACTURE

CROSS-REFERENCE TO CO-PENDING APPLICATION

This application is a divisional filing of the parent application of the same title having U.S. patent application Ser. No. 08/939,753, filed Sep. 29, 1997 U.S. Pat. No. 5,957,850.

BACKGROUND OF THE INVENTION

1. Field of the Invention

This invention relates to ultrasound transducers, and more particularly to phased array ultrasound transducers for use particularly in the medical and diagnostic fields.

2. Brief Description of the Prior Art

Ultrasound machines are widely used for observing internal organs in the human body. Physically, these machines contain ultrasound transducer arrays for converting electrical signals into acoustic pressure waves and vice versa. Generally, the ultrasound transducer array is in the form of a hand-held probe which may be positioned and oriented to direct the ultrasound beam to the region of interest.

The size and limited field of view of existing general purpose ultrasound transducers limit their utility in surgical applications and in applications in which the transducer probe must be inserted into a body cavity. There are regions in the anatomy that cannot be reached using general purpose transducers, and in those regions that can be reached, the field of view is limited to about 90°.

Thus, it is desirable to provide an ultrasound transducer probe that has a field of view greater than existing ultrasound transducers. It is also desirable to provide an ultrasound transducer having dimensions that allow it to be used in surgical and diagnostic applications where there is limited access.

SUMMARY OF THE INVENTION

The present invention fulfills the need in the art for an ultrasound transducer having a field of view greater than 90°, and having a physical shape which permits it to be employed in the investigation and observation of the anatomy, or other body or object, having limited access.

In accordance with the invention, there is provided a plurality of ultrasound transducer arrays, each having a field of view defining an image plane, wherein the axis of each transducer array lies within its corresponding defined image plane.

Preferably, the plurality of transducer arrays are nonaxially aligned and positioned end-to-end with the image planes of all transducer arrays coincident, and with each transducer array having a field of view of about 90°, whereby a resulting combined field of view greater than 90° is produced.

The ultrasound transducer assembly may comprise a housing with a first transducer array arranged at the tip of the housing distal end for acquiring an ultrasound image forward of the distal end, and a second transducer array arranged on a side of the housing distal end for acquiring an ultrasound image laterally of the distal end. The invention may comprise more than two transducer arrays for acquiring ultrasound images in a variety of selectable directions.

More particularly, the invention may comprise an elongated pencil-sized housing having distal and proximal ends, a first transducer array arranged adjacent the housing distal end for acquiring an ultrasound image in a first image plane and with a first field of view of about 90°, and a second transducer array arranged adjacent the housing distal end for acquiring an ultrasound image in a second image plane and with a second field of view of about 90°, the first image plane being coplanar with the second image plane, and the second field of view overlapping the first field of view, resulting in a combined field of view of about 180°.

The proximal end of the pencil-sized housing may be attached to a cable, the cable being connected internally to the first and second transducer arrays, the other end of the cable being connected to a multi-contact connector for attachment to an ultrasound system console. Alternatively, the ultrasound transducer assembly may have a contact terminal, or plug, at its proximal end which is insertable into a hand-held receptacle, the receptacle being connected to the ultrasound system console through a multi-conductor cable.

Methods of manufacture for various preferred embodiments of the invention will be described.

BRIEF DESCRIPTION OF THE DRAWING

These and other aspects of the invention will be better understood, and additional features of the invention will be described hereinafter having reference to the accompanying drawings in which:

FIG. 2 is a perspective side view of one embodiment of the invention in which the pencil-sized ultrasound transducer is attached to the end of a multiple coaxial conductor cable leading to an imaging system console;

FIG. 3 is a top view of the end of the ultrasound transducer shown in FIG. 2 depicting the field of view patterns produced;

FIG. 4 is a perspective view of a receptacle assembly attached to a multiple coaxial conductor cable leading to the imaging system console;

FIG. 5 is a perspective view of a pencil-sized ultrasound transducer module receivable in the receptacle assembly of FIG. 4 attached to a cable leading to the imaging system console;

FIG. 6 is a side view of the ultrasound transducer module shown in FIG. 5;

FIG. 7 is a top view of the ultrasound transducer module shown in FIG. 5, with the distal end of the transducer module shown in partial cross section;

FIG. 15 is a view showing the assembly of both the front and lateral looking acoustic transducer subassemblies;

FIG. 16 is a left side view of the combined front and lateral looking acoustic transducer subassemblies of FIG. 15;

FIGS. 18–21 illustrate an interconnection scheme for the termination of coaxial conductors to a printed wiring board within the pencil-sized transducer as shown in FIG. 2, FIG. 18 showing the coaxial conductor interconnect side of the printed wiring board;

FIG. 19 shows the flex circuit interconnect side of the printed wiring board of FIG. 18;

FIG. 20 is a fragmentary perspective view of the interconnections between the printed wiring board of FIG. 19 and a flex circuit leading to one of the transducer arrays;

FIG. 21 is a fragmentary perspective view of the termination of coaxial conductors to the printed wiring board of FIG. 18 within the pencil-sized ultrasound transducer housing;

FIGS. 22, 23, 24, 25, 26 and 27 illustrate an interconnection scheme for interconnecting the flex circuits leading to the transducer arrays, with the printed wiring board leading to the transducer interconnect extension, or plug, for the pencil-sized transducer module shown in FIG. 5, FIG. 22 showing the contact pad side of the printed circuit board and the connected flex circuit from the lateral looking transducer array;

FIG. 23 is a side view of the arrangement shown in FIG. 22;

FIG. 24 shows the back side view of the plug and the connected flex circuit leading to the front looking transducer array;

FIG. 25 is a view similar to that of FIG. 22 with the flex circuit and lateral looking transducer array removed;

FIG. 26 is a view similar to that of FIG. 23 with the flexible circuits and both lateral and front looking transducer arrays removed;

FIG. 27 is a view similar to that of FIG. 24 with the flex circuit and front looking transducer array removed;

FIG. 28 is a partial cross sectional view of a front looking bi-stack transducer;

FIG. 29 shows one of the flex circuit and transducer array subassemblies for the front looking bi-stack transducer shown in FIG. 28;

FIG. 30 is a back side view of the flex circuit and transducer array subassembly shown in FIG. 29;

FIG. 31 is a partial cross sectional view of a front looking tri-stack transducer;

FIG. 35 shows the flex circuit and front looking transducer array subassemblies for the front looking tri-stack transducer shown in FIG. 31;

FIG. 36 is a left side view of the front looking transducer array subassembly shown FIG. 35;

FIG. 37 is a back side view of the flex circuit and front looking transducer array subassembly shown in FIG. 35;

FIG. 39 shows, schematically, the sequence and spacial positions of transmitted acoustic beams from a transducer with front and lateral transducer stacks; and FIG. 40 shows, schematically, the interception of acoustic energy reflected from an object, by both transducer stacks of a bi-stack transducer.

DETAILED DESCRIPTION OF THE PREFERRED EMBODIMENTS

Figure 1:
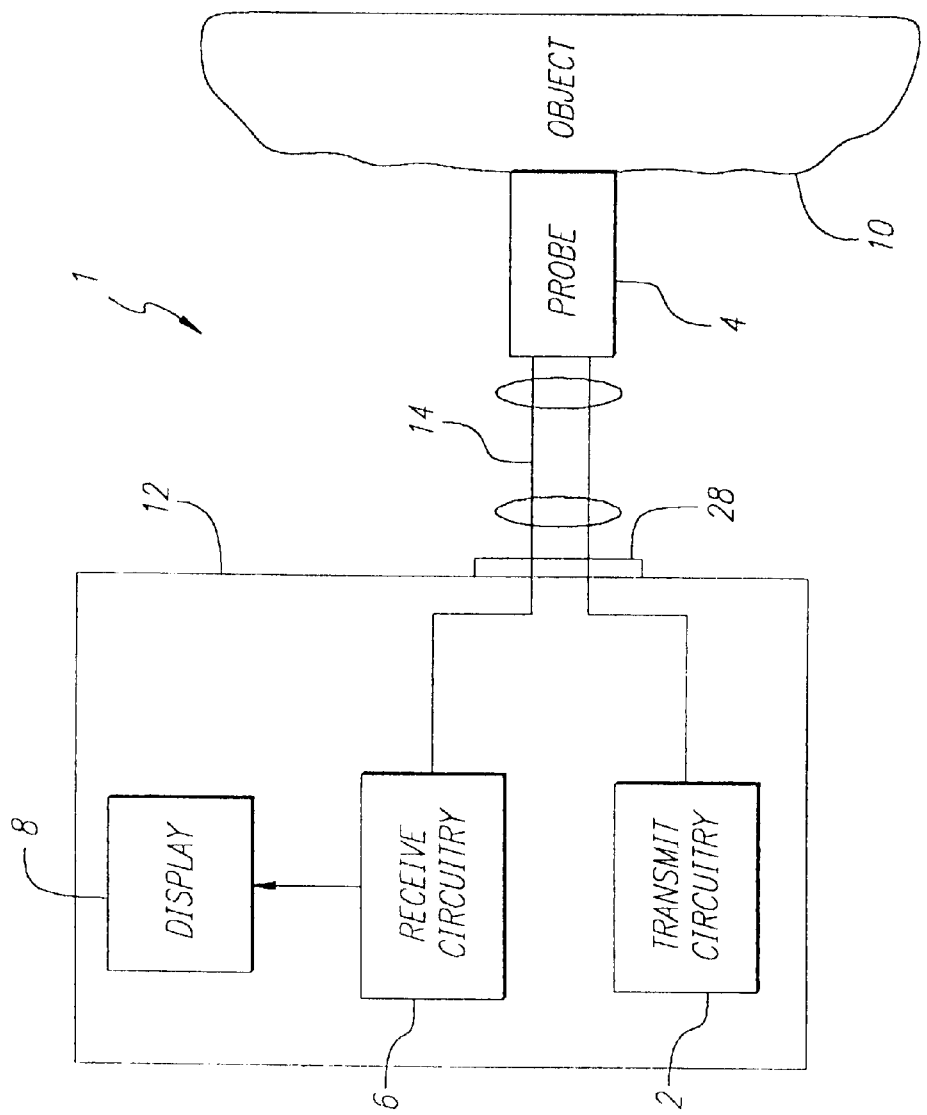
FIG. 1 is a schematic block diagram of an ultrasound system for generating an image of an object or body being observed.

FIG. 1 is a schematic block diagram of an ultrasound system 1 for generating an ultrasound image of an object or body 10 being observed. The ultrasound system 1 includes a system console 12 containing transmit circuitry 2 for transmitting electrical signals to an ultrasound transducer probe 4, receive circuitry 6 for processing signals received by the ultrasound transducer probe 4, and a display 8 for providing a visual image of the object or body 10 being observed. A multiple coaxial conductor cable 14 connects the ultrasound transducer probe 4 to the system console 12 via a system connector 28.

FIG. 2 depicts one embodiment of the invention in which an imaging pencil-sized ultrasound transducer probe 18 is permanently attached to the end of a multiple coaxial conductor flexible cable 14 leading to the imaging system console 12. Elastomeric strain reliefs 24 and 26 are supplied at the probe end and console end, respectively, of the multiple coaxial conductor cable 14. The system end of the cable 14 is connected to a system connector 28 which is mechanically and electrically coupled to the system console 12 by manipulating a locking actuator 30 of known design, such as the ITT Cannon "DL" Series.

The pencil-sized transducer probe 18 is shown to have a pair of imaging phased transducer array stacks 46 and 48 positioned at the distal end of the transducer probe 18, the phased array stack 46 forming an imaging plane of generally trapezoidal shape toward the distal end of the transducer probe 18, and phased array stack 48 producing a lateral looking imaging plane of generally trapezoidal shape, the image planes from both transducer stacks lying in a common imaging plane 22.

The formation of the combined imaging planes from the two imaging ultrasound transducer array stacks 46 and 48 is best observed by reference to FIG. 3 which is a fragmentary top plan view of the end of transducer probe 18 shown in FIG. 2. In FIG. 3, the image plane from stack 46 has an approximate 90° field of view 41 forwardly of the probe 18, while the transducer array stack 48 produces a laterally directed imagine plane having a field of view 43 of approximate 90° and slightly overlapping with the field of view 41 from the front looking array stack 46.

The individual transducer elements of each of the transducer arrays 46,48 on the front and lateral stacks can be electrically excited with different amplitude and phase characteristics to steer and focus the ultrasound beam. An example of a phased array acoustic imaging system is described in U.S. Pat. No. 4,550,607 issued Nov. 5, 1985 to Maslak et al. and is specifically incorporated herein by reference. U.S. Pat. No. 4,550,607 illustrates circuitry for combining the incoming signals received by the transducer array to produce an image on the display screen.

The ultrasound transducer probe of the present invention can be used with existing microcode to provide images from the front or images from the side of the probe. The probe would operate as two separate independent transducer devices in a single housing. However, the ultrasound system can be reprogrammed so that both the front and side images can be displayed simultaneously. Because simultaneous operation of both stacks may present problems, the stacks may be fired alternately.

A wide family of transducer stacks can be utilized to implement the present invention, including linear arrays, trapezoidal imaging arrays, and curvilinear arrays. In a preferred embodiment, trapezoidal sector imaging format is used for each transducer array stack, whereby the field of view from the phased array stack may even exceed 90°. Employing the construction and concepts of U.S. Pat. No. 4,550,607, the field of view may even extend to approximately 110°. For purposes of illustration in this description, however, some phased array stacks will be shown graphically to represent approximately a 90° field of view, and with some slight overlap, the combined field of view will be shown to be slightly less than 180°. Other figures will show greater than 90° fields of view resulting in greater than 180° when combined. Other embodiments will be described which may produce a field of view exceeding 270°.

This extended field of view, well beyond the normal 90°, improves the utility of the transducer probe in surgical applications, and has the added benefit of providing the surgeon or technician with visual imaging of areas adjacent a particular point of interest without having to move the probe and disturb the environment of investigation or cause the patient discomfort. The details of construction and method of manufacturing assembly for a multiple array pencil-sized ultrasound transducer assembly will be described in further detail.

FIG. 4 is a perspective view of a cable assembly 17 connected to an ultrasound imaging system console 12. The cable assembly 17 includes a cable 14, a system connector 28 at one end, and a receptacle 40 at the other end.

FIG. 5 shows a preferred embodiment of a transducer probe module 34 having a coupling plug member 36 which allows the probe module 34 to be coupled to the receptacle 40 of the cable assembly 17. The coupling plug member 36 (hereinafter, plug) has a number of electrical contact pads 38 (schematically represented) on a flat surface thereof which couple to corresponding electrical contacts (not shown) in the body of receptacle 40. Coupling member 36 is shaped to be received in a receptacle slot 40a in the end of receptacle 40, and an actuation lever 39 is provided to electrically and mechanically connect the transducer probe module 34 to the receptacle 40 by pushing down on the actuator lever. Details of an appropriate receptacle assembly for implementing this preferred embodiment of the invention can be found by reference to U.S. Pat. No. 5,617,866 entitled "Modular Transducer System". Details of the coupling member 36 will be described in greater detail hereinafter.

Using the plug and receptacle approach as shown in FIGS. 4 and 5, transducer assemblies with different imaging characteristics can be quickly and conveniently installed into the receptacle during diagnostic procedures. Additionally, the removable probe module 34 may be sterilized without having to sterilize the entire cable assembly 17.

Generally, an ultrasound imaging system is not located in the sterile environment of the operating room. Another advantage of a transducer probe being removable from a receptacle 40 and cable assembly 17 as shown is that the transducer probe 34 can be changed in the sterile environment of the operating room remotely from the ultrasound system. Additionally, being modular, the transducer probe module 34 may be interchanged with another type of transducer probe module using the same cable assembly 17, the same cable connections to the system console, and the same ultrasound system.

Strain reliefs 24 and 26 are provided at the ends of cable 14 as the cable 14 enters the receptacle 40 and system connector 28, respectively. A system connector locking actuator 30, of known design, locks the system connector 28 to the imaging system console 12 mechanically and electrically.

At the distal end of transducer probe module 34, and in accordance with one preferred embodiment of the invention, a front looking transducer imaging subassembly 46 is located at the distal end of the probe module 34, while a similar transducer imaging subassembly 48 is shown to be located laterally of the distal end of the probe module 34. As will be explained in detail later, this arrangement of transducer imaging assemblies provides an improved, expanded, field of view for the diagnostic technician.

FIG. 6 is a side view of the pencil-sized transducer probe module 34 shown in FIG. 5, especially configured for use in surgical and diagnostic applications having limited access.

FIG. 7 is a plan view of the transducer probe 34 shown in FIG. 6 with the distal end of the probe body being shown in partial cross section. The transducer probe 34 has a shaft 40 that is preferably cylindrical in shape. An acoustic lens 20 covers the lateral end adjacent the tip of the probe 34, and an acoustic lens 22 covers the distal end of the probe 34. If desired, lenses 20 and 22 may be manufactured as a single lens member having a right angle cross sectional configuration and made of silicon rubber or urethane polymer.

At the opposite end of the transducer probe module 34 is the coupling plug member 36, being preferably flat and rectangular in shape. It can be seen in FIG. 7 that the plug 13 has a plurality of electrical contact pads 38 which connect to a corresponding plurality of traces on a flex circuit leading to the transducer assembly at the distal end of the probe 34, the details of which will be described hereinafter. When the plug 36 is connected to the receptacle 40 (FIG. 4), the electrical contacts 38 on the plug member 13 make contact with the cable leads from the ultrasound system.

In the cutaway segment of FIG. 7, a thin film ground plane 42 is visible, beneath which ground plane 42 a large plurality of flex circuit traces (not visible in FIG. 7) are positioned, such traces leading to the lateral transducer stack assembly 48 which creates a 90° field of view 70. As will be fully described in connection with other drawing figures, a second flex circuit and an associated ground plane are provided for the transducer stack assembly 46 at the end of the probe shaft 40, producing a 90° field of view 68. The respective 90° fields of view 68, 70 preferably overlap one another to produce a combined field of view approaching 180°.

Figure 8:
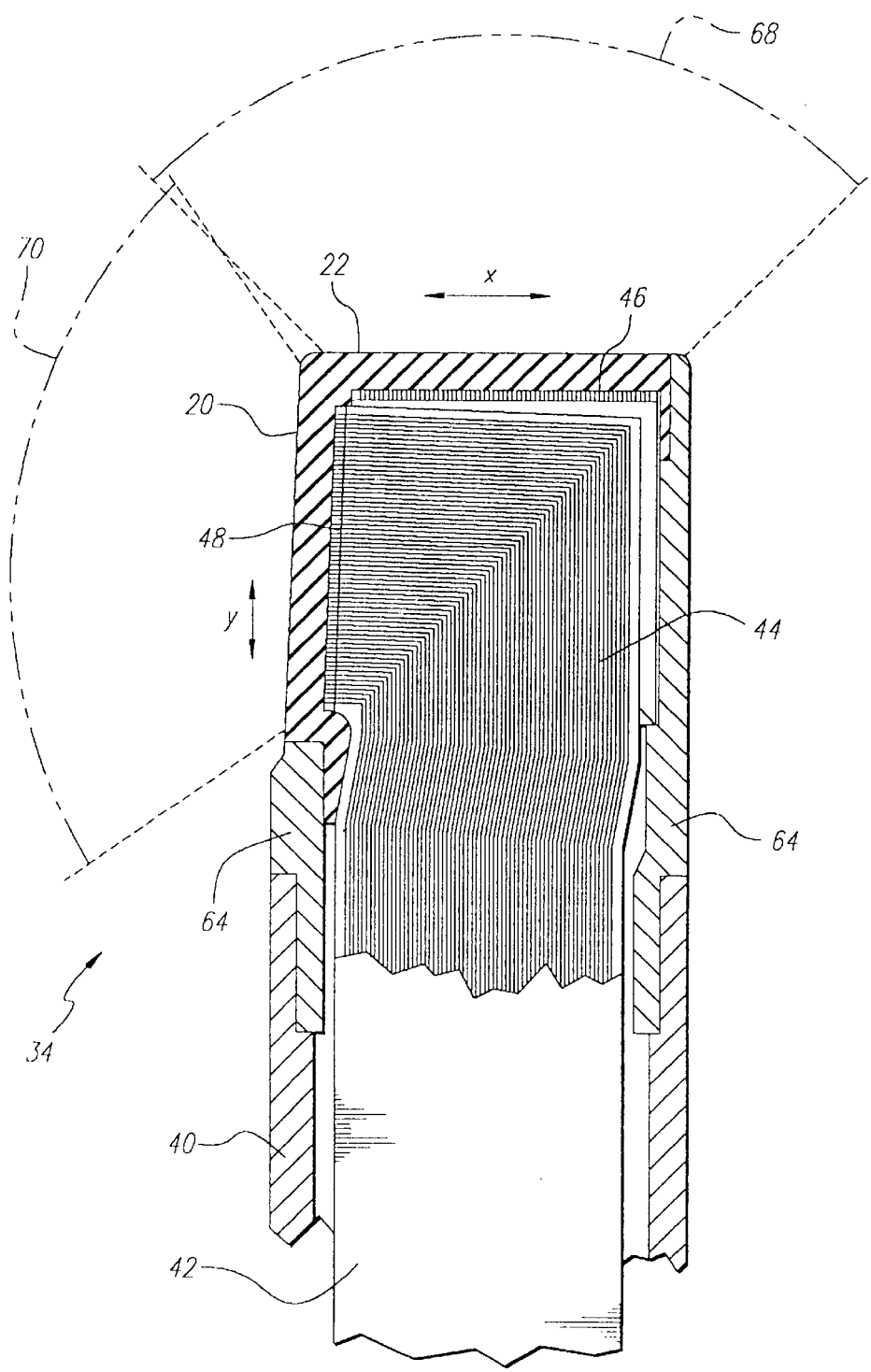
FIG. 8 is a cross sectional view of the end of an ultrasound transducer probe of the present invention in FIG. 6 showing an arrangement of front and lateral looking bi-stack transducer arrays.

In FIG. 8, the housing shaft 40 of the transducer probe module 34 is shown in cross section, the shaft 40 providing a housing for the interior components of the transducer probe 34. At the distal end of shaft 40, a Radel™ plastic nose piece 64 is affixed, nose piece 64 mounting the acoustic lenses 20, 22. Such construction permits the acoustic lenses 20 and 22 mounted to the nose piece 64 in a separate operation, and the assembled nose piece and lens combination may then be conveniently and easily fixed to the distal end of shaft 40, oriented in the proper relationship to the orientation of the plug 36.

Within the cross sectional view of FIG. 8, the exposed end portion of the transducer probe 34 shows the positions of the front looking transducer array 46 and the lateral looking transducer array 48. For convenience, in this description, the front looking transducer array stack will be referred to hereinafter as the front stack 46, while the lateral looking transducer array stack will be referred to as the lateral stack 48.

In FIG. 8, it will be noted that the lateral lens 20 is angled slightly inwardly toward the end of probe 34, such that its field of view 70 overlaps the field of view 68 produced by the front stack 46. As mentioned, the front and lateral stacks operate on the principle of phased array acoustic imaging which produces a generally trapezoidal shaped field of view of approximately 90°, such that the combined field of view as shown in FIG. 8 will approximate 180°. Also as mention previously, using trapezoidal sector imaging, a field of view approaching 110° is possible, thereby making the combined field of view for the FIG. 8 configuration of the present invention approaching 220° as a practical limit.

Each transducer stack 46, 48 is preferably comprised of sixty-four piezoelectric transducer elements, and in FIG. 8, such elements would be elongated elements having a direction into the page across the front and lateral side at the distal end of probe 34. In order to provide electrical connection to each of the sixty-four transducer elements of each front and lateral stack 46, 48, multiple trace flex circuits may be used. For example, a flex circuit 44 with sixty-four individual parallel traces are connected to the sixty-four transducer elements of the lateral tack 48, and the traces on the flex circuit 44 are led toward the connector end of the probe 34 in a manner to be described hereinafter.

The flex, or flexible, circuit 44 may be, for example, any interconnecting design used in the acoustic or integrated circuit field. A suitable flexible circuit is manufactured by Sheldahl of Northfield, Minn. The flexible circuit is typically made of polyimide material, typically KAPTON™, upon which a plurality of copper signal traces are bonded, the traces carrying the signals for exciting individual transducer elements. The individual piezoelectric transducer elements are connected to the ends of the copper signal traces, each signal trace terminating at a center pad, also preferably formed of copper, upon which center pad each transducer element is disposed and connected. The interconnect center pads may be gold plated to improve the contact performance. Preferably, the center pads are coextensive in size with the electrode of the transducer element.

The transducer elements of the front and lateral looking stacks are sequentially arranged in the direction parallel with the plane of the paper as shown by arrows Y and X in FIG. 8. Preferably, there are sixty-four elements in each transducer array, and each transducer element of the array disposed on the front and lateral stacks 46, 48 will have a width as represented by the arrow W in FIG. 16.

To establish a transmission line effect for the traces on flex circuit 44, to protect the traces on flex circuit 44 from the induction of noise, either from the environment or from the body under investigation, and to minimize cross talk or other effects due to coupling of signals from the traces, a ground plane 42, insulated from the signal traces, is connected to system ground and covers the traces all the way up to the connection of the individual traces to the transducers on the front stacks 46. In FIG. 8, the ground plane 42 is shown cut away in order to illustrate the routing of signal traces on flex circuit 44 leading to the lateral stack 48. In FIG. 8, only the lateral stack flex circuit 44 is visible. The front stack flex circuit is beneath.

Figure 11:
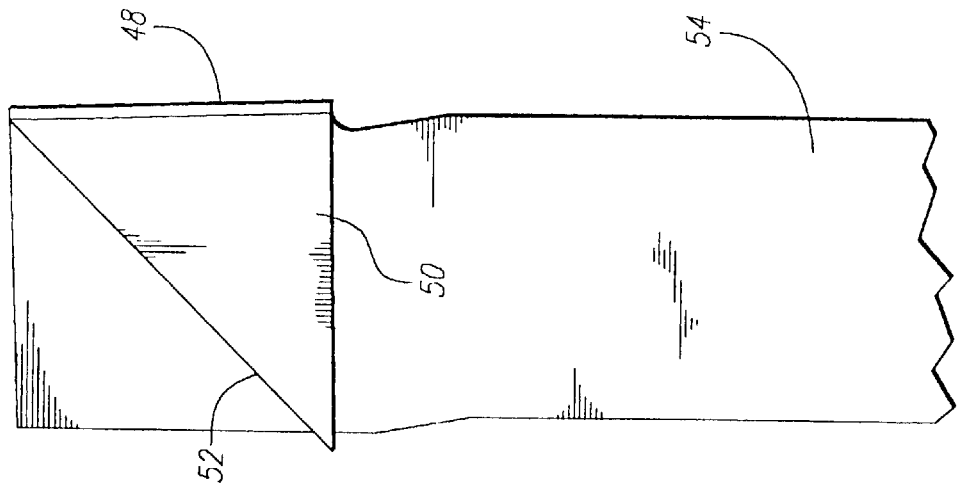
FIG. 11 is a back side view of the lateral looking acoustic transducer subassembly as shown in FIG. 9.
Figure 10:
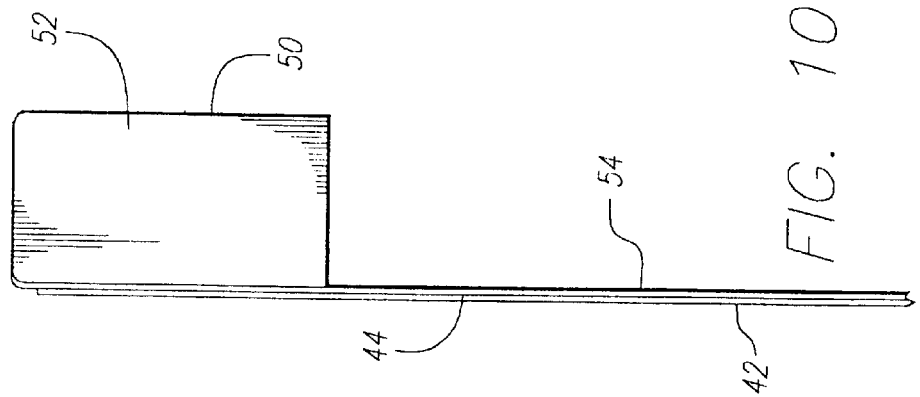
FIG. 10 is a right side view of the lateral looking acoustic transducer subassembly as shown in FIG. 9.
Figure 9:
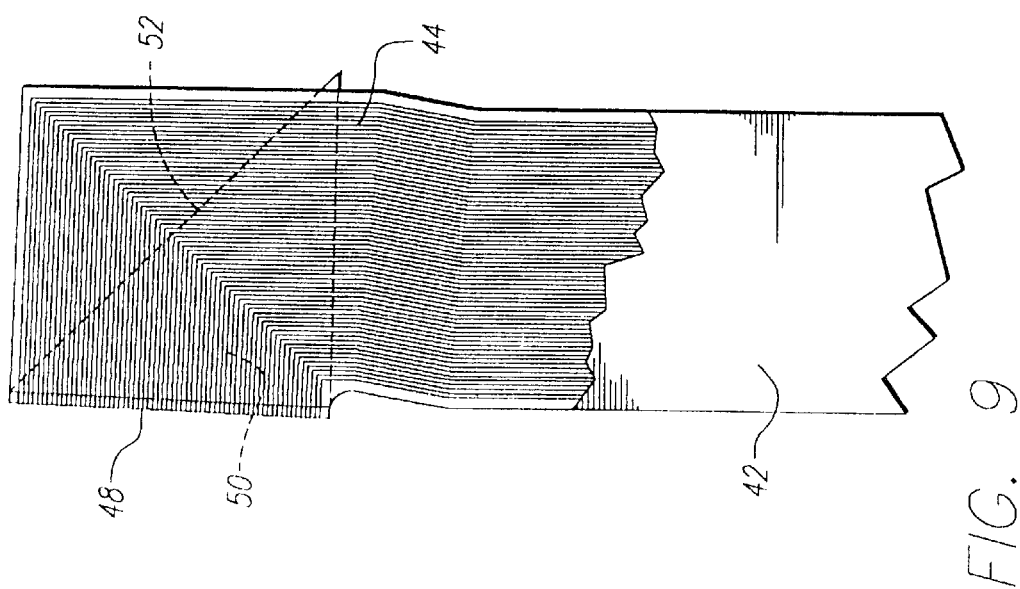
FIG. 9 shows a flexible circuit connected to the lateral looking acoustic transducer subassembly.

FIG. 9 illustrates the lateral acoustic transducer stack subassembly comprising the lateral stack 48, the flex circuit 44, the ground plane 42, and, in phantom, the backing block 50 seen in FIGS. 10 and 11.

In FIG. 10, a right edge view of the subassembly shown in FIG. 9, it will be observed that the backing block 50, against which the flex circuit 44 lies, has a back edge 52. The back side 54 of flex circuit 44 is a thin dielectric film upon the other side of which the traces of flex circuit 44 are formed.

FIG. 11 is a rear view of the lateral acoustic subassembly shown in FIG. 9, and in this view, the triangular wedge shape of backing block 50 is observable. The back edge 52 of backing block 50 is seen to define the hypothenuse of the right triangular cross section of backing block 50. The piezoelectric elements of lateral stack 48 are represented in FIG. 11 on the right side of backing block 50 as shown.

It will be understood that, since the plane of the lateral stack 48 is to be tilted slightly inwardly at the probe end, in order to keep the back edge 52 at a 45° angle, the lateral side of the wedge-shaped backing block 50 will be slightly shorter than the rearward side. Maintaining the angle of back edge 52 at 45° is essential for purposes of mating with the backing block of the front looking acoustic subassembly to be described with reference to FIGS. 12–14.

Alternatively, as mentioned, fields of view up to about 110° are possible, such that the front stack 46 and lateral stack 48 may be arranged orthogonally. One advantage of this configuration is that the backing blocks 50, 58 can be manufactured identically.

Figure 14:
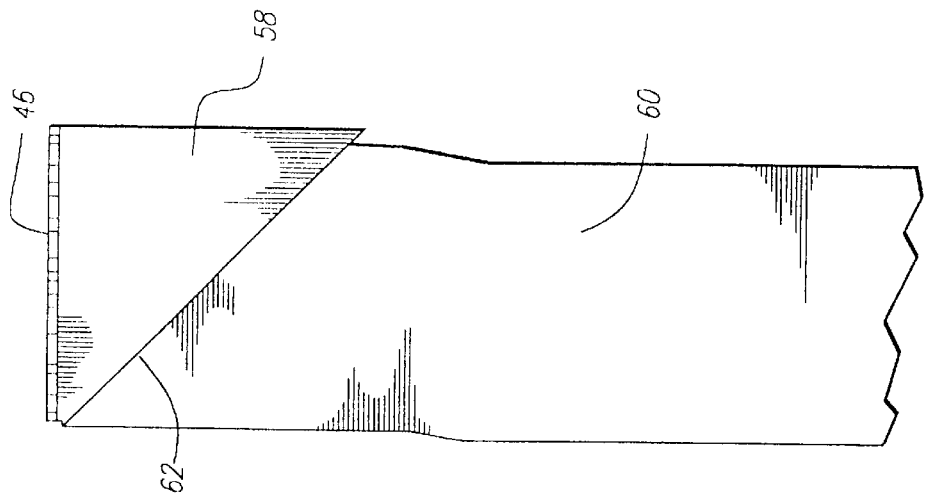
FIG. 14 is a back side view of the front looking acoustic transducer subassembly as shown in FIG. 12.
Figure 13:
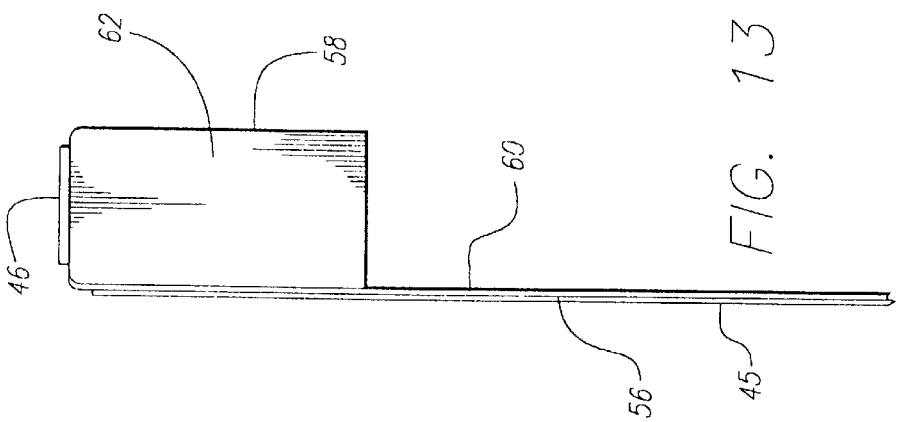
FIG. 13 is a right side view of the front looking acoustic transducer subassembly as shown in FIG. 12.
Figure 12:
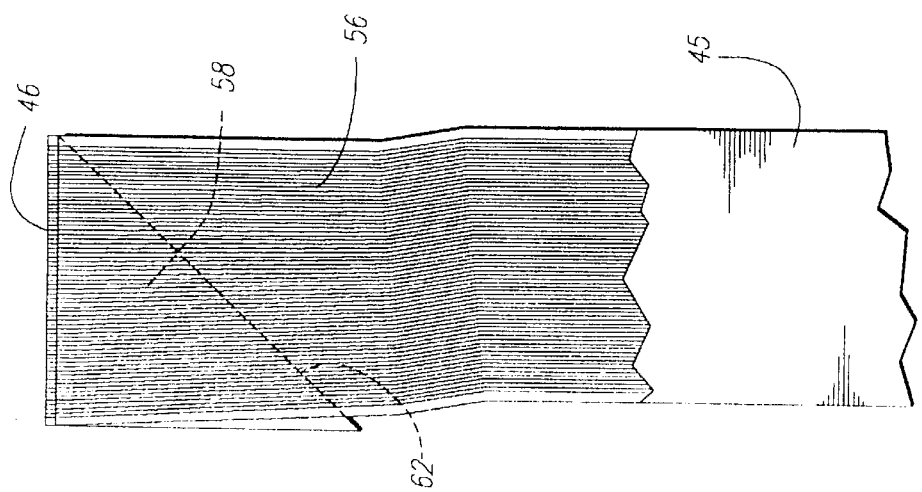
FIG. 12 shows a flexible circuit connected to the front looking acoustic transducer subassembly.

FIG. 12 illustrates the front acoustic transducer stack subassembly comprising the front stack 46, the flex circuit 56, the ground plane 45, and, in phantom, the backing block 58 seen in FIGS. 13 and 14.

In FIG. 13, a right edge view of the subassembly shown in FIG. 12, it will be observed that the backing block 58, against which the flex circuit 56 lies, has a back edge 62. The back side 60 of flex circuit 56 is a thin dielectric film upon the other side of which the traces of flex circuit 44 are formed.

FIG. 14 is a rear view of the front acoustic subassembly shown in FIG. 12, and in this view, the triangular wedge shape of backing block 58 is observable. The back edge 62 of backing block 58 is seen to define the hypothenuse of the right triangular cross section of backing block 58. The piezoelectric elements of front stack 46 are represented in FIG. 14 at the top of backing block 58 as shown.

FIG. 15 is a composite drawing showing the internal workings of the probe 34 absent the shaft housing 40, the nose piece 64, and the lenses 20, 22. In this figure, the angular relationship between the front stack 46 and the lateral stack 48 will be appreciated.

FIG. 16 is a left side view of the arrangement shown in FIG. 15. In this figure, the elongated piezoelectric transducer elements making up the lateral stack 48 are visible, and their lengths are shown relative to the thickness of the backing block 50. The front stack 46 is shown in edge perspective in FIG. 16, but has the same physical appearance in plan view as that shown for lateral stack 48.

Referring to the group of FIGS. 8–16, the front looking acoustic subassembly of FIGS. 12–14 is similar in design to the lateral acoustic subassembly of FIGS. 9–11, except that the front stack backing block 58 is substantially the mirror image of the lateral backing block 50. Additionally, the signal traces of the front stack flex circuit 56 do not turn 90°. Instead, they extend upon the flex side of the backing block 58 and over the top surface of backing block 58 as can be seen in FIG. 13.

The front stack 46 and lateral stack 48 are assembled together back-to-back to form the transducer assembly shown in FIGS. 8, 15, and 16. In particular, the angular back edge 62 of the front stack 46 and the angular back edge 52 of the lateral stack 48 are mated together so that both angular surfaces are in surface contact along their entire length. Both angular back edges 52 and 62 are preferably machined to provide precision flat surfaces for bonding the backing blocks 50, 58 together. Preferably, an adhesive, more preferably an epoxy adhesive, is first applied to the angular back edge 52 of the lateral stack 48. The front stack 46 is then positioned in place with angled edges 52 and 62 in contact, and the front stack 46 is slid along the mutually engaging surfaces 52 and 62 until a predetermined alignment of the two transducer stacks is achieved. When coupled in this way, a single square or rectangular backing block results. As so assembled, the emitting surfaces of the transducer arrays of the front and lateral stacks 46, 48 are substantially perpendicular to one another.

Referring back to FIG. 8, the front and lateral stacks 46, 48, after assembled and bonded together, are placed in the housing shaft 40 with the emitting surfaces of the transducer arrays exposed. The acoustic lenses or windows 20, 22 are fixed at one end and at a position on one side of the nose piece 64. The nose piece 64, with the lenses 20, 22 affixed thereto is then placed in the end of housing shaft 40. Bonding of the lenses 20, 22 to the nose piece 64, and bonding of the nose piece 64 to housing shaft 40 may be effected by epoxy bonding or other adhesive or cohesive bonding, sonic weld bonding, or any other bonding technique which tightly seals the connections.

Because the invention preferably employs trapezoidal sector imaging format for each transducer stack, it is preferable to fire each array independently temporarily. Otherwise, the circuitry required to operate both (or all) arrays simultaneously becomes quite complicated. Considering that the backing blocks 50 and 58 are highly attentive, i.e. substantially absorptive of ultrasound energy radiated in its direction away from an object of interest, a synergistic effect is realized by placing the backing blocks with their back edges bonded together. That is, the active array has its own backing block plus the other backing block to absorb ultrasound energy directed behind the array, thereby minimizing acoustic artifacts in signals supplied to the ultrasound imaging system.

In a preferred embodiment, each transducer element has a width W (see FIG. 16) of about 3 millimeters. Preferably, the diameter of the housing shaft 40 is about 10 millimeters. Also, preferably, each signal trace of the flex circuits 44, 56 has a width of about 0.05 millimeters and the spacing between signal traces is about 0.05 millimeters. Since each transducer array has sixty-four transducer elements, the flex circuits 44, 56 will each have sixty-four signal traces.

In a preferred embodiment, the backing blocks 50, 58 are formed of a filled epoxy comprising Dow Corning's part number DER 332 treated with Dow Corning's curing agent DEH 24 and has an aluminum oxide filler. In a preferred embodiment, the piezoelectric layer is composed of lead zirconate titanate (PZT). However, it may be formed of composite material or polymer material (PVDF).

Figure 17:
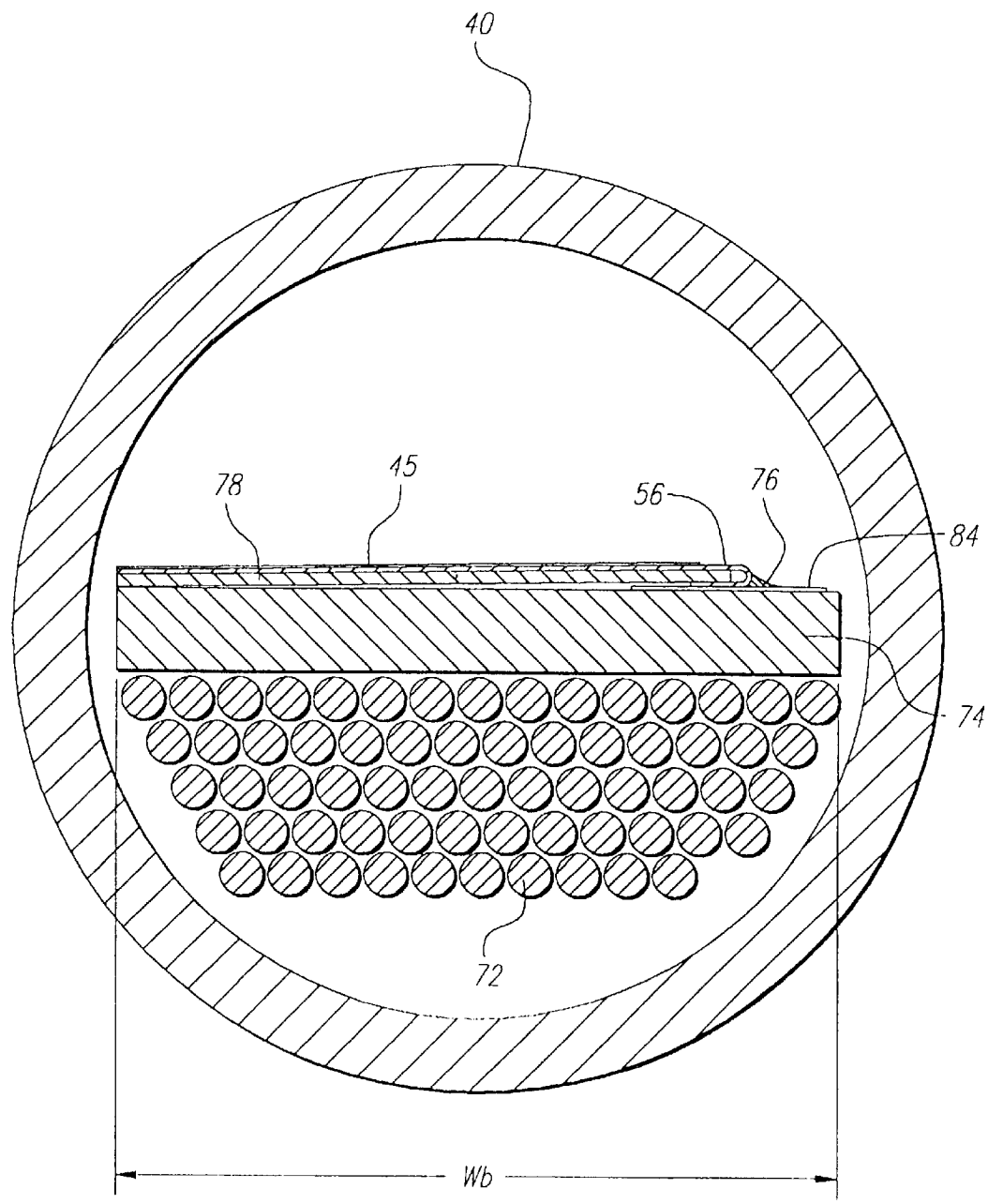
FIG. 17 is a cross sectional view of an intermediate portion of the pencil-sized transducer module taken along the lines 17—17 in FIG. 2.

FIG. 17 is a cross section of the transducer probe 18 in the interconnect area within shaft 40, the view taken along the lines 17—17 in FIG. 2.

As viewed in FIG. 17, the preferred cross sectional configuration for the shaft 40 is shown to be cylindrical having an outside diameter preferably of about 9.8 millimeters and an inside diameter preferably of about 8.3 millimeters.

Although a pencil-sized ultrasound transducer employing the concepts of the present invention may be structured in a variety of configurations, the accompanying drawings show two physical embodiments, and the description to follow is also limited to these two embodiments. However, it will be understood that many different physical body configurations may be envisioned for implementing the pencil-sized ultrasound transducer.

In accordance with a first embodiment, the self-contained transducer assembly of FIG. 2 requires, within the transducer probe 18, termination of multiple coaxial conductors within cable 14, such cable terminations being required to electrically connect the coaxial conductors of cable 14 to individual transducer elements via the aforementioned flex circuits.

The embodiment of FIGS. 4 and 5, on the other hand, terminate the multiple coaxial conductors in cable 14 within receptacle 40, and the coupling plug member 36 need only be provided with a plurality of electrical contact pads 38 to make appropriate connections to the multiple coaxial conductors of cable 14 within receptacle 40. However, the transducer probe module 34 shown in FIG. 5 would thus require, within housing shaft 40, multiple connections between the flex circuits 44 and 56 coupled to the front and lateral stacks 46 and 48, and the electrical contact pads 38. To accomplish this, the coupling member 36 takes the form of a printed wiring board having the electrical contact pads 38 being carried through the printed wiring board to within the housing shaft 40 for connection with the flex circuitry.

Accordingly, in the description to follow, both the self-contained unit of FIG. 2 and the modular configuration of FIGS. 4 and 5 will be described separately insofar as connection to the cable 14 to the front and lateral stacks 46, 48 are concerned.

As mentioned, FIG. 17 is a cross section of the self-contained pencil-sized ultrasound transducer assembly of FIG. 3, and therefore shows sixty-four 40-gauge coaxial conductors 72 of the system cable 14 on one side of an interconnect printed wiring board 74 (having a width of approximately 7.5 millimeters), and the flex circuit arrangement 73 on the opposite side of the printed wiring board 74.

Details of the connection between the multiple coaxial conductors 72 and the flex circuit arrangement 73 will become clearer in the description to follow. The general configuration of the flex circuit arrangement 73 can be appreciated by reference to FIG. 17, in which a 0.0125 millimeter thick stiffener 78 lies on top of the interconnect printed wiring board 74 providing a support for the flex circuit 56 with its ground plane 45 being on top. The interconnect printed wiring board 74 has a number of interconnect pads 84 which are mechanically and electrically connected to corresponding ends of the traces on flex circuit 56 by standard solder bridges 76, typically on 0.75 millimeter centers.

Since the view seen in FIG. 17 is forward of the transducer probe 18 shown in FIG. 2, the termination of sixty-four of the coaxial conductors 72 will have been interconnected with their corresponding traces on flex circuit 44 rearwardly of the cross sectional position. It will be understood, however, that a similar arrangement as that shown in FIG. 17 would be visible toward the proximal end of transducer probe 18 with sixty-four additional coaxial conductors 72 in the space above flex circuit arrangement 73, and with a corresponding flex circuit arrangement positioned on the underside of a second interconnect printed wiring board 74, again rearwardly within transducer probe 18.

FIGS. 18 and 19 show, respectively, the coaxial conductor interconnect side 75 and the flex circuit interconnect side 77 of interconnect printed wiring board 74 shown in FIG. 17. As mentioned, two of these interconnect printed wiring boards 74 are required, each providing an interconnection between sixty-four coaxial conductors and associate flex circuit arrangements for the two separate front and lateral stacks. FIGS. 18 and 19 thus show only one of such printed wiring boards.

Alternatively, a single long printed wiring board (not shown) may be preferred, on which all 128 coaxial conductors connect with 128 traces on the flex circuits.

Both sides of the printed wiring board 74 have ground plane copper layers 49 and 51 on the coaxial and flex circuit sides 75, 77, respectively. On the coaxial conductor side 75, the ground plane copper layer 49 is etched away in two locations for the placement of thirty-two coaxial conductor interconnect pads 78, 80 at one edge of the printed wiring board 74. Representative coaxial conductors 82 are shown schematically in FIG. 18, the details of which will follow. A pair of holes 76 is provided at the ends of printed wiring board 74 for aligning the printed wiring board 74 with corresponding alignment holes (not shown) on the flex circuits. With alignment pins (not shown) passing through both sets of holes, precise alignment of the interconnect pads 78 and traces on the flex circuits 44, 56 is achieved to ensure solid and reliable solder connections.

The flex circuit interconnect side 77 of printed wiring board 74 shown in FIG. 19 shows the sixty-four flex interconnect older pads 84 all along one edge of the printed wiring board 74 opposite the edge for connection of the coaxial conductors. Not shown, but well understood by one of ordinary skill in the art, the circular shaped pads shown in FIGS. 18 and 19 represent via holes in the printed wiring board 74, the via holes connected to intermediate traces within printed wiring board 74 leading from the sixty-four coaxial conductor interconnect pads 78 to corresponding ones of the flex interconnect solder pads 84.

Figure 20:
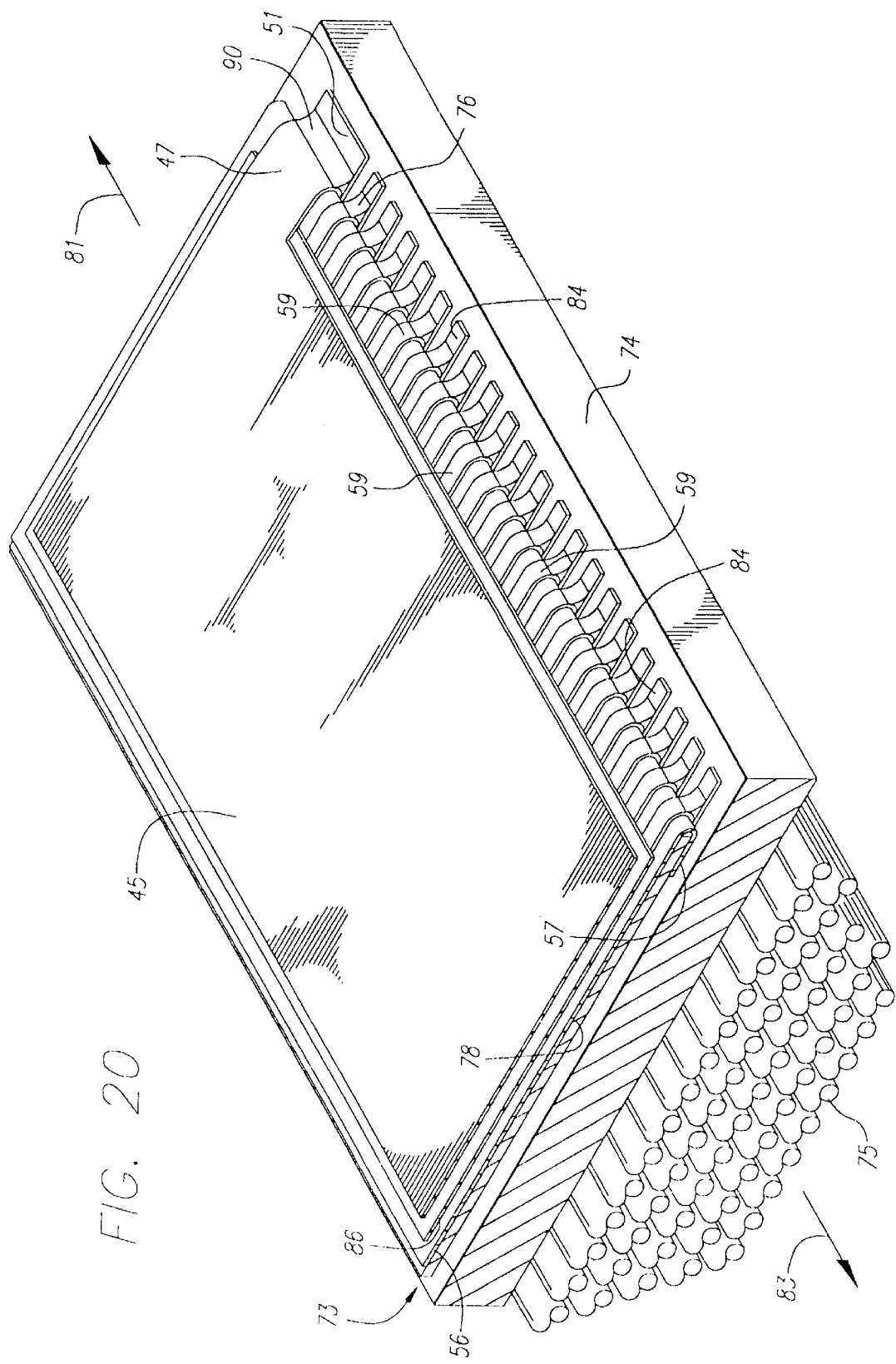

FIG. 20 is a perspective view of a segment of the printed wiring board 74 and the associated coaxial conductors 72 and flex circuit arrangement 73 on opposite sides of the printed wiring board 74. In comparing FIG. 20 with other figures, it should be noted that the acoustic stacks are located in the direction of arrow 81, and the cable en of the arrangement shown is in the direction of arrow 83.

Preferably, printed wiring board 74 is an epoxy-glass laminate with an etched copper layer bonded thereto forming interconnect pads 84 as described in connection with FIG. 19. The flex circuit arrangement 73 is shown to have an exterior ground plane layer 45, spaced from the signal traces 59 of flex circuit 56 by a dielectric spacer 86. The ground plane 45 stops short of interfering with the individual traces 59 of the flex circuit 56. The flex circuit 56 has a wrap around edge 57 wrapped around the right edge (as seen in FIG. 20) of stiffener 78, the series of traces 59 being precisely aligned with corresponding interconnect pads 84 on the printed wiring board 74. Mechanical and electrical connections between the individual traces 57 and interconnect pads 84 are provided by a corresponding number of solder bridges 76.

The copper ground plane 45 has a lateral extension 47 wrapped around the end of stiffener 78 but spaced from the last interconnect pad 84 on the printed wiring board 74. As seen in FIG. 19, the copper ground plane layer 51 of printed wiring board 74 extends the length of the board 74 and lies adjacent both ends of the series of interconnect pads 84. As shown in FIG. 20, the extension 47 of ground plane 45 is, like the wrap around edge 57 of flex circuit 56, wrapped around the stiffener 78, and a rather large solder bridge 90 mechanically and electrically connects the ground plane extension 47 of the flex circuit to the ground plane copper layer 51.

Figure 21:
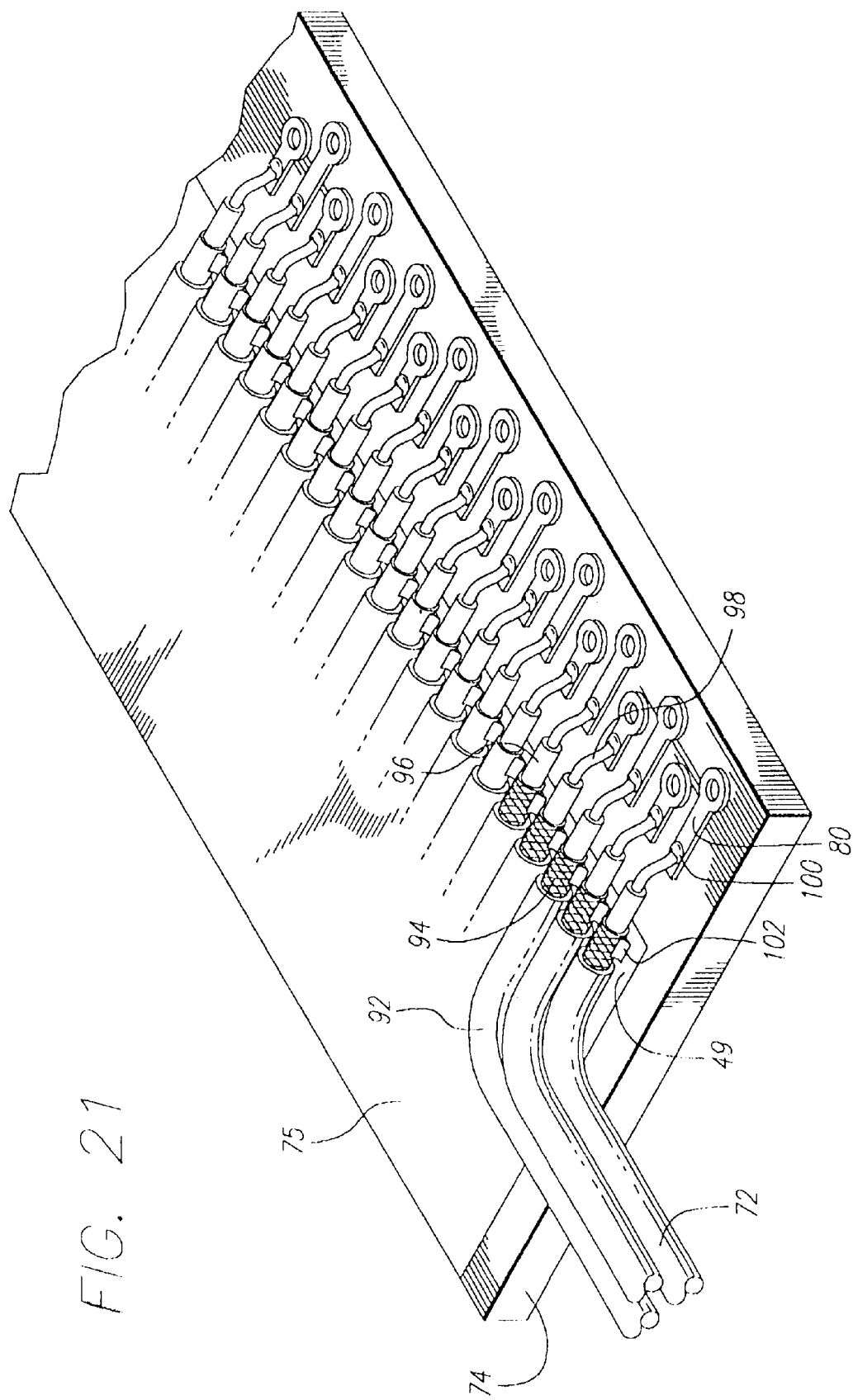

In FIG. 21, a representative number of coaxial conductors 72 are shown lying on the termination, or interconnect, side 75 of the printed wiring board 74. Each coaxial conductor 72 comprises an outer conductor insulator 92, a conductor shield 94, an inner conductor dielectric 96, and a signal conductor 98. The conductor shield 94 of each coaxial conductor 72 is soldered at 102 to the ground plane 49 (see FIG. 18), and the signal conductor 98 of each coaxial conductor 72 is soldered to a corresponding termination/interconnect pad 80 (see FIG. 18) at solder termination 100.

Reference is now made to FIGS. 22–27 showing the interconnection between flex circuits from the front and lateral stacks 46, 48 to a printed wiring board 110 leading to the coupling plug member 36 of the modular transducer probe 34 shown in FIG. 5.

FIG. 22 illustrates in more detail the electrical contact pads 38 on the contact pad side of coupling plug member 36. In this figure, the flex circuit 44 from the lateral stack 48 is shown to be connected at sixty-four places along one edge of the printed wiring board 110. As seen in FIGS. 22, 23, and 25, sixty-four flex circuit interface pads 112 are arranged along the edge of printed wiring board 110. The flex circuit 44 is wrapped around a stiffener (not shown) in a manner similar to that shown and described in connection with FIG. 20, such that sixty-four solder bridges 114 electrically and mechanically interconnect between the flex circuit traces and the printed wiring board 110.

FIG. 23 is a side view of the arrangement shown in FIG. 22, this figure showing the lateral flex circuit arrangement 71 coupling the printed wiring board 110 to the lateral stack 48, and the front stack flex circuit arrangement 73 coupling the printed wiring board 110 to the front stack 46.

FIG. 23 also shows the flex circuit stiffener 78 (of FIG. 17) for front stack flex circuit arrangement 73, and a corresponding flex circuit stiffener 87 for the lateral flex circuit arrangement 71. The copper ground plane layers 53 and 55 for the contact pad side and back side of printed wiring board 110 shown in FIGS. 22 and 24, respectively, extend end-to-end of printed wiring board 110 with the exception that it is etched away for isolation from the contact pads 38 and the strip of interface pads 112, 120, 116, and 122 on both sides of printed wiring board 110.

FIG. 24 is a representation similar to that of FIG. 22, but showing the front stack assembly, i.e. Flux circuit arrangement 73 connecting the piezoelectric elements of front stack 46 to sixty-four corresponding printed wiring board interconnect pads 116 soldered to the traces of flex circuit 56 at solder bridges 118.

FIGS. 25–27 show the printed wiring board 110 layout and construction without the flex circuit arrangements attached. The printed wiring board 110 is preferably a multilayer printed wiring board with 6 layers each about 0.8 millimeters thick. This configuration for the printed wiring board 110 will permit reasonable sized internal copper traces in the 6 layers to route the signals from flex circuit interface pads 112 and 116 to corresponding contact pads 38 on coupling plug member 36. The circular pads shown connected to flex circuit interface pads 112 and 116, and the series of circular pads 120 and 122 on the respective opposite sides of printed wiring board 110 represent via holes for connecting the copper traces on the layers of printed wiring board 110 between the interface pads 112, 116 to the electrical contact pads 38.

The embodiments of the invention described to this point involve a pair of ultrasound transducer arrays arranged at the distal end of a pencil-sized housing and having a front field of view and a lateral field of view which, when combined, provide an extended angular field of view of approximately 180°. In the front looking and lateral looking bi-stack transducer arrangement shown for example in FIG. 8, the center of the image produced by the transducer is directed 45° to the port side of the transducer. While this may be beneficial in observing, for example, the walls of an organ into which the pencil-sized transducer is inserted, in other applications, a 180° field of view having a center directed forwardly of the transducer may be preferred. FIGS. 28–30 provide such an embodiment.

In FIG. 28, a housing shaft 130 mounts, at its end, a nose piece 132 mounting a unitary lens member comprising lens 138 and 142, behind which are positioned a port side looking ultrasound transducer stack 136 and a starboard side looking ultrasound transducer stack 140, respectively. In this figure, it should be observed that the fields of view 137, 139 for the stacks 136, 140 are greater than 90°. As a result, even with an overlapping of the fields of view 137, 139, the combined field of view is greater than 180°, a practical limit being about 220°.

This construction results in a centerline of the combined field of view to be forward of the distal end of the transducer probe, defining a front looking bi-stack transducer 129.

The construction of the front looking bi-stack transducer is made possible by the provision of a pair of backing blocks 146, 152 having their back edges 148,150 bonded together along a centerline of the housing shaft 130. A flex circuit 134 is shown in FIG. 29 to feed the port side stack 136, while a flex circuit (not visible) feeds the piezoelectric elements of the starboard stack 140. FIG. 30 shows the backside 144 of flex circuit 134 and the shape and positioning of the backing block 146. It will be appreciated by reference to the phantom lines in FIG. 29 that the mirrored construction of a starboard flex circuit arrangement (not shown) will result in the back edges 148 and 150 being in axial alignment with the housing shaft 130. All other function and structural features common to the front and lateral looking bi-stack transducer of FIGS. 8–15 equally apply to the front looking bi-stack transducer of FIGS. 28–30. Accordingly, a full representation of the entire bi-stack arrangement of the front looking transducer is not necessary.

One advantage of a front looking bi-stack transducer constructed as shown in FIGS. 28–30 is that both acoustic stack subassemblies are identical, resulting in reduced manufacturing and assembly costs.

The pencil-sized ultrasound transducer according to the present invention is not restricted to only a bi-stack configuration. Any number of transducer stacks may be combined in a physical layout to produce any desired field of view range, including a field of view of 360°. For all practical purposes, however, a 360° field of view would be neither necessary nor practical, since part of the field of view would include the body of the transducer itself causing acoustic reflections which could introduce unwanted artifacts in the signal representing the image of the body being investigated.

One practical multi-stack transducer, however, is shown in FIGS. 31–37 in which 3 transducer stack subassemblies are arranged orthogonal to one another at the imaging tip of the transducer 160. In FIG. 31, the front looking tri-stack transducer 160 comprises a housing shaft 162 fitted with a nose piece 164 to which a 3-sided lens member is attached, the lens member comprising lenses 168, 172, and 176. Behind lenses 168, 172, and 176, are corresponding transducer array stacks 166, 170, and 174. The generally trapezoidal shaped field of view patterns for the three transducer stacks 166, 170, 174 are shown as fields of view 178, 180, and 182, respectively. Since each trapezoidal field of view is shown to exceed 90°, even with overlapping the fields of view as shown, the total combined field of view for the front looking tri-stack transducer 160 is greater than 270°, a practical limit being 330°.

Figure 34:
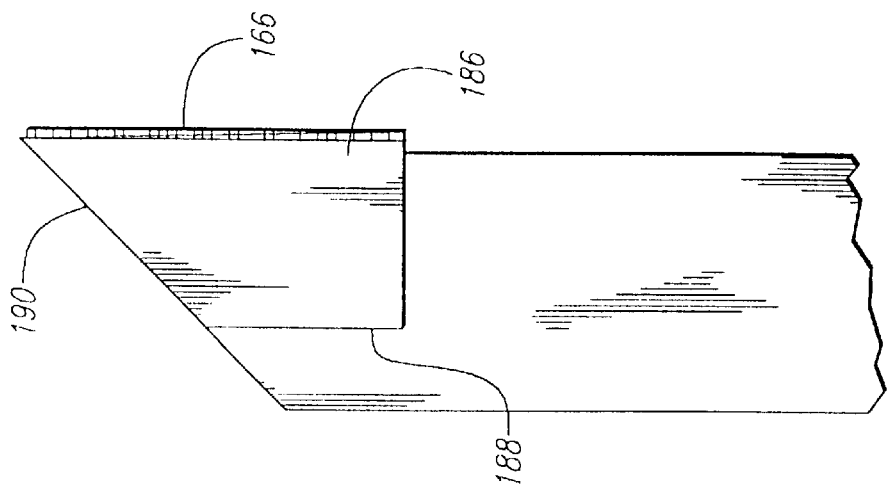
FIG. 34 is a back side view of the flex circuit and lateral looking transducer array subassembly shown in FIG. 32.
Figure 33:
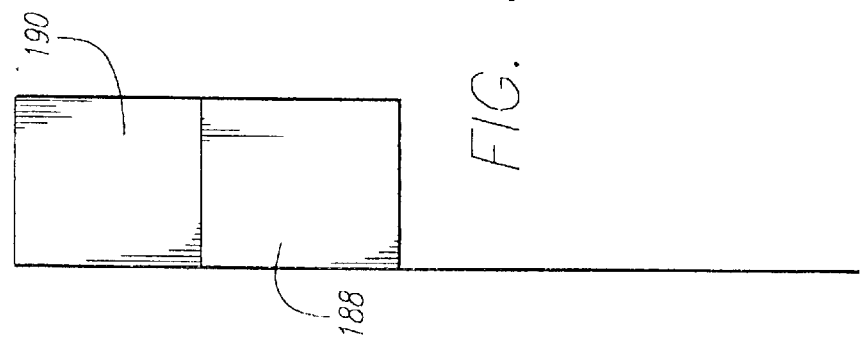
FIG. 33 is a right side view of the lateral looking transducer array subassembly shown FIG. 32.
Figure 32:
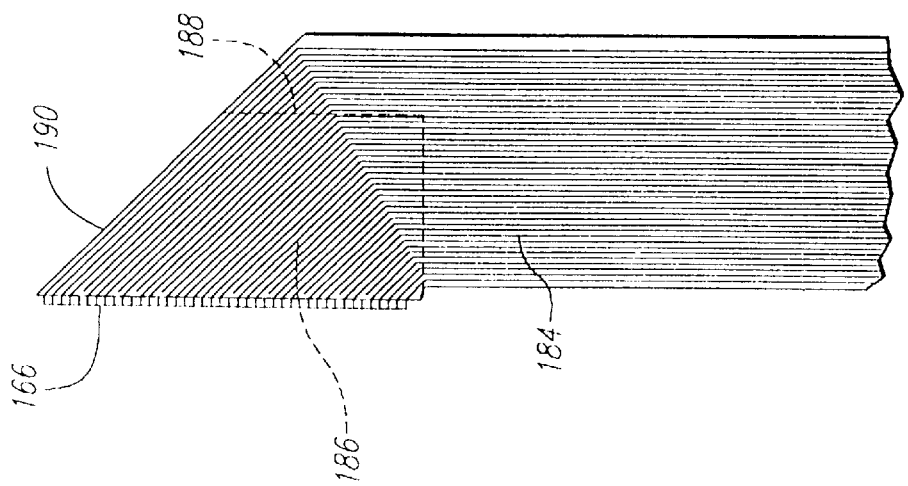
FIG. 32 shows one of the flex circuit and lateral looking transducer array subassemblies for the front looking tri-stack transducer shown in FIG. 31.

To construct the front looking tri-stack transducer 160, two identical lateral acoustic stack subassemblies are required as shown in FIGS. 32–34. FIG. 32 shows the port side lateral transducer stack 166 being fed by a flexible circuit 184. The flex circuit 184 is supported by a backing block 186 which has two machined back edge surfaces 188 and 190, as best seen in FIGS. 33 and 34.

The front looking acoustic stack subassembly is shown in FIGS. 35–37. The front looking stack 170 is fed by a flex circuit 196 which flares outwardly to connect with the individual transducer elements of the stack 170.

For case of illustration the required ground planes for the flex circuits in FIGS. 31–37 are not shown.

As best seen in FIGS. 36 and 37, a triangular shaped backing block 191 supports the front looking acoustic stack 170 and has machine surfaced back edges 192 and 194. In assembling the tri-stack transducer, the pair of identical lateral acoustic stack subassemblies of FIGS. 32–34 are assembled back-to-back with their back edges 188 in surface contact and bonding together. The front acoustic stack of FIGS. 35–37 is then brought into assembly with the lateral acoustic stack subassemblies with the machined edges 192 and 194 in surface contact with and bonding to the corresponding back edges 190 of the lateral acoustic stack subassemblies.

As additional background information, a review of some ultrasound imaging basics follows, particularly directed to a method for generating ultrasound images from two (or more) ultrasound stacks, both (all) on one plane.

Generating Ultrasound Energy

Very small thickness variations of piezoelectric crystal can be caused by subjecting it to an electrical field across its thickness. The appropriate electrical signal to electrodes on opposite surfaces of the crystal will cause ultrasonic energy to be generated. This energy is transferred into the object of interest (e.g., a human body) by mechanical coupling. Piezoelectric crystals can convert electrical signals into acoustic energy and can also convert intercepted acoustic energy back into electrical signals.

Ultrasound Beam Formation

The ultrasound energy from a linear array of piezoelectric crystals can be concentrated on a specific structure in space (azimuth and range) by controlling the times at which the crystals transmit (see FIG. 39). The circuitry which controls the transmitting process is, in general, incorporated into the imaging system; the process is called beamforming because it can cause the transducer to emit radial "beams" of acoustic energy into an object, such as a human body.

At a particular instant of time when the ultrasound energy originating from the multitude of crystals converges on a structure of interest, a reflection occurs having unique properties, relative to reflections from its surroundings, due to the differences in acoustic properties of the structure relative to its surroundings. The structure effectively becomes the source for a spherical "front" of ultrasound energy which radiates in all directions; this energy is intercepted by each individual piezoelectric crystal in the linear array.

Reception of Ultrasound Energy From the Structure

The amount of energy and the time at which it is received by each crystal is determined by the crystal location (distance and angle) relative to the reflective structure. By introducing appropriate delays and amplifications into the electrical signal path from each crystal, then combining the signals, a reinforced electrical representation of the structure can be generated.

Scanning the Imaging Field

One common method of acquiring the data required to reconstruct an image of structures within the body is to transmit one beam, or line, using all of the piezoelectric crystals in the array as transmitters, then to receive reflected ultrasound energy using all the piezoelectric crystals as receivers. The amplification factors and the delays introduced into the data stream from each receiver is optimized to observe structure where the transmitted beam was focused. Upon reception of all the data for one beam, the next beam is transmitted into the body along a slightly different radial path, the receivers optimized for that beam, etc. This sequential scanning of the field with transmitted beams, together with the corresponding receiving activity, causes the entire field of view of about 90 degrees to be covered.

Display of the Structure

A pictorial representation of a structure can be generated by manipulating the data before sending it to a raster display (cathode ray tube or liquid crystal display). The image is generated from received data for each ultrasound line (beam) which is transmitted; the radial pattern of diverging ultrasound lines leads to a trapezoidal imaging pattern of the structures encountered by the ultrasound beams. To generate the image, a regular sequence of beams are generated from one side of the volume of interest to the other side.

Normal Ultrasound Format

Generally, the transducer incorporates a linear array of individual and independent piezoelectric crystals; the image generated is trapezoidal in shape.

Generating an Image Using More Than One Transducer Array Stack

If two transducer stacks radiating into the same plane are orthogonal to each other, one of two methods can be used to generate an image which displays structure from more than the normal 90 degree field of view. Each method addresses the potential ambiguity which can be caused by energy from one stack intercepted by both.

Figure 38:
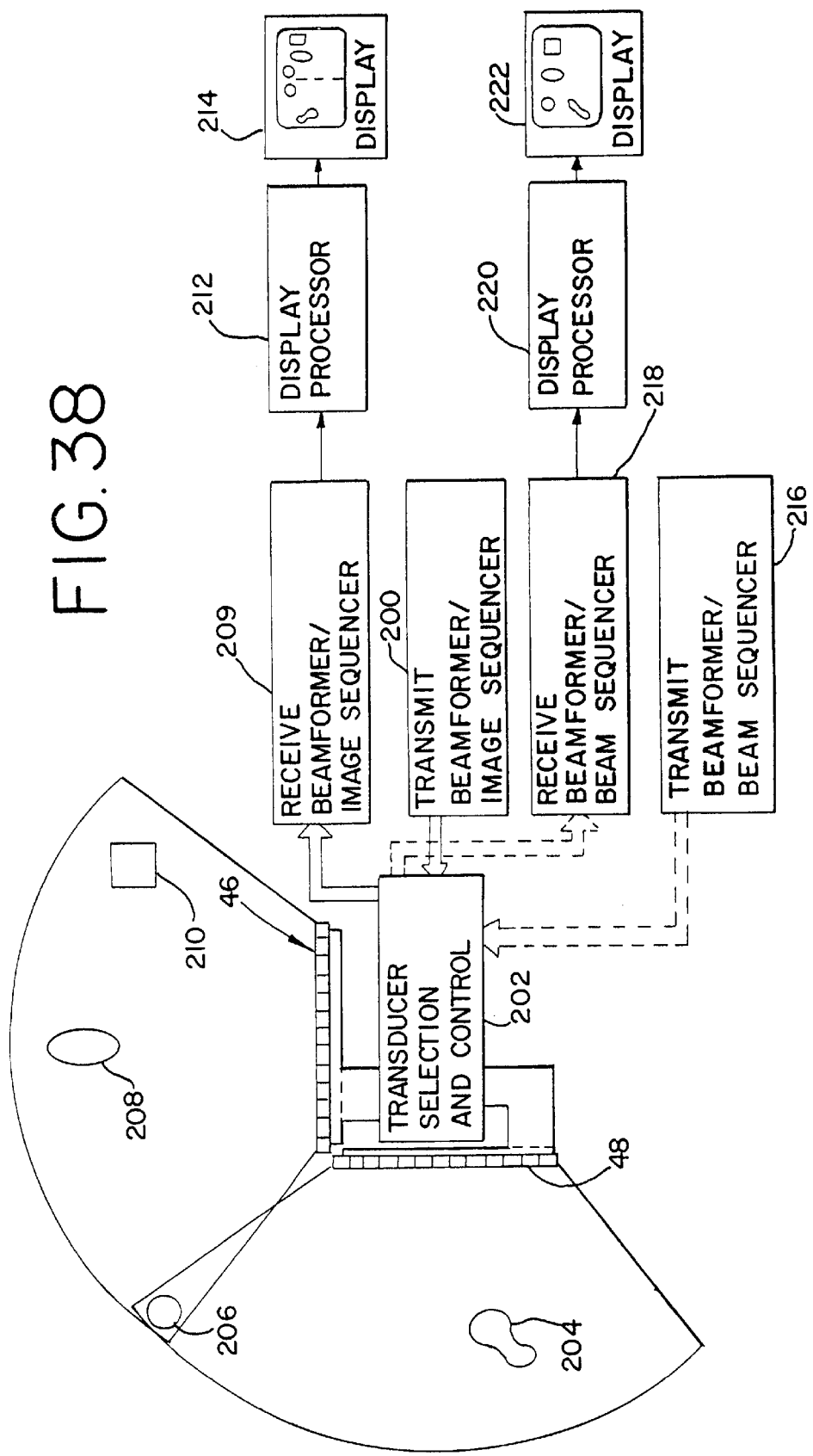
FIG. 38 is a circuit block diagram showing functional blocks for generating an image on a display using a transducer having more than one transducer array stack.

The first method depends on displaying sequentially the independently generated image from each stack. With reference to FIGS. 38–40, one display image represents the structure in the field of view of lateral stack 48, while another display image represents the structure in the field of view of front stack 46. Since alternate images, or frames, are generated and displayed at different times, there is no ambiguity of data from the receivers; data as a result of the energy transmitted by lateral stack 48 is not detected by front stack 46, because front stack 46 is "blind" during the interval of time that lateral stack 48 is being used, etc.

The first method may be performed using the block diagram and solid lined circuit paths of FIG. 38 which shows a pair of orthogonally disposed transducer array stacks, lateral stack 48 and front stack 46. An image sequencing transmit beamformer 200, through transducer selection and control block 202, sends appropriate signals to lateral stack 48 and front stack 46 to create independent and alternate beam scans of the respective fields of view. The field of view of lateral stack 48 includes objects 204 and 206, while the field of view of front stack 46 includes objects 206, 208, and 210. A receive beamformer image sequencer 209 alternately presents the independently generated images from lateral stack 48 and front stack 46 to a display 214 through a display processor 212. Display processor 212 effects desired display characteristics such as brightness, image and motion enhancement, color, etc.

The display 214 thus displays objects 204 and 206 on the left side of the display screen and objects 206, 208, and 210 on the right side of the display screen. Although object 206 is displayed in both screen presentations, each object in each display half is scanned with transmitted energy, and the reflected energy is analyzed, all by the same transducer stack. That is, the circuitry for lateral stack 48 never processes reflected acoustic energy originating from front stack 46, and vice versa. In this respect, the presentation on the display monitor 214 is not unlike the imaging of independent transducer stacks, the only difference being that the electronics of FIG. 38 time shares the two image generating transducer stacks and presents the resulting images side-by-side on a display monitor.

As to the second method, reference is now made to FIGS. 39 and 40 in which FIG. 39 shows a transducer 222 generating a sequence of transmit beams 224 from the lateral-facing transducer stack 48 and a continuing sequence of transmit beams 224 from the front looking transducer stack 46, thereby forming a continuous 180° field of view 226. The second method involves sequentially transmitting ultrasound beams 224 into the body from the bottom to the top of lateral stack 48, then from the left to the right of front stack 46. The beamformer thus causes the linear arrays of piezoelectric crystals to generate ultrasound beams 224 which are transmitted into the body over an angle on the order of 180° degrees.

As illustrated in FIG. 40, reflected ultrasound energy 230 from structure 206 within the body, regardless of whether the transmitted source of acoustic energy is from lateral stack 48 or front stack 46, is likewise intercepted by individual piezoelectric crystals in both stacks. By optimizing the receiver amplifications and delays, taking into account the geometry of the two stacks, a receive data stream using piezoelectric crystals in both stacks is thus acquired.

The beam sequencing method just described may be implemented using the block diagram and dashed line circuit paths shown in FIG. 38, i.e., the transducer selection and control block 202 is connected through the dashed lines instead of the solid lines in the figure. The field of view pattern shown in FIG. 38 is replaced by the field of view pattern shown in FIG. 39 in this second method. The transducer selection and control block 202 thus effects the beam generation sequence as described starting with the bottom transducer element of lateral stack 48 and ending with the right most transducer element of front stack 46 in a continuous sequence of beamforming to create the approximately 180 degree field of view. As opposed to sequencing alternating images for display on display monitor 214, circuit blocks 216 and 218 perform the transmit and receive beamforming with each field of view defined by a continuous sequencing of transmitted beams 224 across both stacks.

Employing this second method, a beam sequencing transmit beamformer 216, through transducer selection and control block 202, sends appropriate signals to lateral stack 48 and front stack 46 to create continuous beam scans across the two stacks. The transmitted beams from lateral stack 48 impinge objects 204 and 206, while the transmitted beams from front stack 46 impinge objects 208 and 210. In the second method, as seen in FIG. 39, it will be observed that the transmission fields of view of lateral stack 48 and front stack 46 do not overlap, resulting in a presentation on display monitor 222 of the entire 180 degree field of view as if a single transducer array stack generated it.

In the beam sequencing receive beamformer 218, it will be observed from FIG. 40 that the signal received from the right most crystal element of front stack 46 must have the most gain and the least delay of all of the transducer elements in front stack 46, while the signal from the left most crystal element of front stack 46 must have the least gain and most delay of all the transducer elements in front stack 46 in order to define a received reflected ultrasound beam from structure 206. Display processor 220 effects desired display characteristics such as brightness, image and motion enhancement, color, etc.

The display 222 thus displays objects 204, 206, 208, and 210 as if a single 180 degree field of view was generated by a single transducer stack.

FIGS. 38–40 have dealt with the transmission and receiving of ultrasound energy from two stacks substantially orthogonally disposed. As presented herein, an extension of the circuit of FIG. 38 and the analysis of FIGS. 38–40 involving more than two transducer stacks would apply and be readily evident to a person of ordinary skill in the art after understanding the details of these figures. In this connection, reference is made to U.S. patent application Ser. Nos. 08/286,658, 08/432,615, and 08/434,160, and to PCT International Publication No. WO 96/04568, all of which are incorporated herein by reference. These references explain in great detail transmit and receive beamforming technology. It is presumed that the person of ordinary skill in the art to which the present invention pertains is familiar with and can apply the principles set forth in these references of prior art where appropriate and necessary in the understanding of the present invention.

While only certain embodiments of the invention have been set forth above, alternative embodiments and various modifications will be apparent from the above description and the accompanying drawing to those skilled in the art. For example, for the probe module 34 of FIG. 5, coaxial conductors may be used to connect the contact pads 38 to the flex circuits 44, 56, instead of using printed wiring board connections. Alternatively, the printed wiring board 110 may serve to directly connect all transducer elements to respective contact pads on the coupling plug member 36 without employing flex circuits. These and other alternatives are considered equivalents and within the spirit and scope of the present invention.

What is claimed is:

1. An ultrasound transducer imaging system interface for use with an ultrasound imaging system having data processing means and display means, said display means displaying data processed by said data processing means as a continuous series of video frames, said interface comprising:

a plurality of transducer imaging stacks each producing independent data representing corresponding coplanar independent fields of view of a region of interest; and an interface processor for processing data from each said imaging stack independently for display, by said display means, on alternate video frames, images of said region of interest within respective alternate coplanar independent fields of view.

2. The interface of claim 1 wherein the images within respective alternate coplanar independent fields of view are displayed in combined field of view greater than 90 degrees.

3. An ultrasound transducer imaging system interface for use with an ultrasound imaging system having data processing means and display means, said display means displaying data processed by said data processing means as a continuous series of video frames, said interface comprising:

a plurality of transducer imaging stacks;

a beam sequencing transmit beamformer arrangement coupled to said plurality of transducer imaging stacks for producing a continuous sequence of acoustic beams transmitted into a region of interest from said plurality of transducer imaging stacks;

a beam sequencing receive beamformer arrangement for producing a data stream representing intercepted acoustic energy reflections from said region of interest originating from all of said plurality of transducer imaging stacks; and an interface processor for processing said intercepted acoustic energy reflections, and for displaying, by said display means on each frame, an image of said region of interest within the combined fields of view of said imaging stacks.

4. The interface of claim 3 wherein the combined fields of view comprises a fields of view greater than 90 degrees.

5. A method of imaging using ultrasound transducers and an ultrasound imaging system having data processing means and display means, said display means displaying data processed by said data processing means as a continuous series of video frames, said method comprising:

producing from each of a plurality of transducer imaging stacks each producing independent data representing corresponding coplanar independent fields of view of a region of interest; and processing data from each said imaging stack independently for display, by said display means, on alternate video frames, images of said region of interest within respective alternate coplanar independent fields of view.

6. The interface of claim 5 wherein the processing comprises displaying the images in a combined field of view greater than 90 degrees.

7. A method of imaging using ultrasound transducers and an ultrasound imaging system having data processing means and display means, said display means displaying data processed by said data processing means as a continuous series of video frames, said method comprising:

producing a continuous sequence of acoustic beams transmitted into a region of interest from a plurality of transducer imaging stacks;

producing a data stream representing intercepted acoustic energy reflections from said region of interest originating from all of said plurality of transducer imaging stacks; and processing said intercepted acoustic energy reflections, and displaying, by said display means on each frame, an image of said region of interest within the combined fields of view of said imaging stacks.

8. The method of claim 7 wherein the processing comprises displaying the images with a field of view greater than 90 degrees.

* * * * *